US007679615B2

(12) United States Patent
Kim et al.

(10) Patent No.: US 7,679,615 B2
(45) Date of Patent: Mar. 16, 2010

(54) CALCULATING THREE-DIMENSIONAL (3D) VORONOI DIAGRAMS

(75) Inventors: Deok-Soo Kim, Seoul (KR); Youngsong Cho, Seoul (KR); Donguk Kim, Gangneung-si (KR)

(73) Assignee: IUCF-HYU (Industry-University Cooperation Foundation Hanyang University), Seoul (KR)

( * ) Notice: Subject to any disclaimer, the term of this patent is extended or adjusted under 35 U.S.C. 154(b) by 855 days.

(21) Appl. No.: 11/120,743

(22) Filed: May 3, 2005

(65) Prior Publication Data

US 2005/0248567 A1    Nov. 10, 2005

Related U.S. Application Data

(60) Provisional application No. 60/567,860, filed on May 4, 2004, provisional application No. 60/568,784, filed on May 6, 2004.

(51) Int. Cl.
*G06T 1/00* (2006.01)
(52) U.S. Cl. .......................................... 345/418; 702/27
(58) Field of Classification Search ........................ None
See application file for complete search history.

(56) References Cited

U.S. PATENT DOCUMENTS

| | | | | |
|---|---|---|---|---|
| 6,182,016 | B1* | 1/2001 | Liang et al. | 702/22 |
| 6,384,826 | B1* | 5/2002 | Bern et al. | 345/441 |
| 6,631,202 | B2* | 10/2003 | Hale | 382/128 |
| 7,050,612 | B2* | 5/2006 | Hale | 382/128 |
| 2003/0149537 | A1* | 8/2003 | Binkowski et al. | 702/27 |
| 2004/0249809 | A1* | 12/2004 | Ramani et al. | 707/4 |
| 2005/0089878 | A1* | 4/2005 | Debe et al. | 435/6 |
| 2005/0192758 | A1* | 9/2005 | Xie | 702/19 |

OTHER PUBLICATIONS

VORO3D. Jun. 8, 2004. http://web.archive.org/web/20040608124835/http://www.lmcp.jussieu.fr/~mornon/voronoi.html.*
Srivastava et al. Analysis of Cocaine Receptor Site Ligand Binding by Three-Dimensional Voronoi Site Modeling Approach. Journal of Medicinal Chemistry. 1993.*
Meng et al. Automated Docking with Grid-Based Energy Evaluation. Journal of Computational Chemistry. vol. 13. No. 4. 1992.*
Ewing et al. DOCK 4.0—Search Strategies for Automated Molecular Docking of Flexible Molecule Databases. Journal of Computer-Aided Molecular Design. 2001.*

(Continued)

*Primary Examiner*—Peter-Anthony Pappas
(74) *Attorney, Agent, or Firm*—Patterson, Thuente, Skaar & Christensen, P.A.

(57) ABSTRACT

Systems and methods for computing three-dimensional (3D) Euclidean Voronoi diagrams are disclosed. For some embodiments, a set of 3D objects is accessed, in which each 3D object is mathematically defined. Thereafter, a Voronoi region associated with each of the 3D objects is computed, thereby resulting in a complete Euclidean Voronoi diagram of the set of 3D objects. In some embodiments, the 3D objects are spheres, each of which is defined by a center and a radius. For other embodiments, the 3D objects are convex objects, each of which is mathematically-definable (e.g., cylinders, sphero-cylinders, etc.). Unlike prior approaches that suggested using a numerical approach to computing the Voronoi diagram, the present disclosure employs mathematical approaches for computing the Euclidean Voronoi diagram, thereby improving efficiency in the computation of the Euclidean Voronoi diagram.

9 Claims, 17 Drawing Sheets

OTHER PUBLICATIONS

DOCK 4.0—User Manual. 1998.*

Boissonnat et al. On the Combinatorial Complexity of Euclidean Voronoi Cells and Convex Hulls of d-dimensional Spheres. Proceedings of the Fourteenth Annual ACM-SIAM Symposium on Discrete Algorithms. 2003.*

Nadassy et al. Standard Atomic Volumes in Double-Stranded DNA and Packing in Protein-DNA Interfaces. Nucleic Acids Research. vol. 29. No. 16. Oxford University Press. 2001.*

Nadassy et al. Structural Features of Protein—Nucleic Acid Recognition Sites. Biochemistry. vol. 38. No. 7. Feb. 1999.*

Conte et al. The Atomic Structure of Protein-Protein Recognition Sites. Journal of Molecular Biology. vol. 285. No. 5. Feb. 1999.*

Gavrilova et al. Updating the Topology of the Dynamic Voronoi Diagram. Computer Adided Geometric Design. 2003.*

DesJarlais et al. Using Shape Complementarity as an Initial Screen in Designing Ligands for a Receptor Binding Site of Known Three-Dimensional Structure. Journal of Medicinal Chemistry. 1988.*

Boulu et al. Voronoi Binding Site Model of a Polycyclic Aromatic Hydrocarbon Binding Protein. Journal of Medicinal Chemistry. 1990.*

Boulu et al. Voronoi Binding Site Models—Calculation of Binding Modes and Influence of Drug Binding Data Accuracy. Journal of Computational Chemisty. vol. 10. No. 5. 1989.*

Bradley et al. Voronoi Modeling—The Binding of Triazines and Pyrimidines to L casei Dihydrofolate Reductase. Journal of Medicinal Chemisty. 1993.*

Luchnikov et al. Voronoi-Delaunay Analysis of Voids in Systems of Nonspherical Particles. 1999.*

Poupon. Voronoi and Voronoi-related Tessellations in Studies of Protein Structure and Interaction. Current Opinion in Structural Biology. vol. 14. Issue 2. Apr. 2004.*

PCT Notification of Transmittal of the International Search Report and the Written Opinion of the International Searching authority, or the Declaration, mailed on Dec. 7, 2005.

Aurenhammer, Franz; "Voronoi Diagrams—A Survey of a Fundamental Geometric Data Structure"; dated Sep. 1991; ACM Computing Surveys, vol. 23, No. 3; pp. 345-405.

Lavender, David; "Voronoi Diagrams of Set-Theoretic Solid Models"; dated Sep. 1992; 1992 IEEE; pp. 69-77.

Gerstein, et al.; "The Volume of Atoms on the Protein Surface: Calculated from Simulation, using Voronoi Polyhedra"; dated 1995; J. Mol. Biol. (1995) 249; pp. 995-966.

Goede, A., et al.; "Voronoi Cell: New Method for Allocation of Space among Atoms: Elimination of Avoidable Errors in Calculation of Atomic Volume and Density"; dated 1997; Journal of Computation Chemistry vol. 18, No. 9; pp. 1113-1123.

Will, Hans-Martin; "Practical and efficient computation of additively weighted Voronoi cells for applications In molecular biology"; dated May 27, 1998; Technical Report #300, Departement Informatik, ETH Zürich; pp. 1-14.

McConkey, B. J., et al.; "Quantification of protein surfaces, volumes and atom—atom contacts using a constrained Voronoi procedure"; dated 2002; Bioinformatics, vol. 18, No. 20, 2002; pp. 1365-1373.

Karavelas, Menelaos I.; "Dynamic additively weighted Voronoi diagrams in 2D"; dated 2002, Lecture Notes in Computer Science, vol. 2461; pp. 586-598.

Kim, Deok-Soo; "Euclidean Voronoi diagrams of 3D spheres and applications to protein structure analysis"; dated 2005; Japan Journal of Industrial and Applied Mathematics, 22(2); pp. 251-265.

Gore, Swanand P., et al.; "Provat: A Tool for Voronoi Tessellation Anslysis of Macromolecular Structures" dated 2005; vol. 00, No. 00; pp. 1-6.

Chong-Min Kim, Youngsong Cho, Byunghoon Lee, Jeongyoun Seo, Sang-Min Park, Chung-In Won, Donguk Kim and Deok-Soo Kim, "Interface surfaces for protein-protein interaction: Voronoi diagram based approach," 2005 CAD/CAM.

Donguk Kim, Youngsong Cho, Deok-Soo Kim, "Algorithms for constructing Euclidean Voronoi diagrams for spheres in 3D: an edge tracing algorithm and a region expansion algorithm," 2005 CAD/CAM.

Deok-Soo Kim, Cheol-Hyung Cho, Youngsong Cho, Donguk Kim, "Pocket recognition on a protein using Euclidean Voronoi diagram of atoms," pp. 1-23.

Deok-Soo Kim, Youngsong Cho, Donguk Kim, Sangsoo Kim, Jonghwa Bhak, Sung-Hoon Lee, "Euclidean Voronoi diagrams of 3D spheres and applications to protein structure analysis," Running Title: Euclidean Voronoi Diagrams of Spheres, pp. 1-22.

V.A. Luchnikov, N.N. Medvedev, L. Oger and J.-P. Troadec, "Voronoi-Delaunay analysis of voids in systems of nonspherical particles," Physical Review E, vol. 59, No. 6, Jun. 1999, pp. 7205-7212.

Deok-Soo Kim, Youngsong Cho and Donguk Kim, "Euclidean Voronoi diagram of 3D balls and its computation via tracing edges," Jan. 31, 2005, pp. 1-28.

Donguk Kim, Deok-Soo Kim, "Euclidean Voronoi diagrams for spheres in 3D by expanding regions," pp. 1-10.

Donguk Kim, Youngsong Cho, and Deok-Soo Kim, "Region expansion by flipping edges for Euclidean Voronoi diagrams of 3D spheres based on a radial data structure".

Deok-Soo Kim, Youngsong Cho, Donguk Kim, "Edge-tracing algorithm for Euclidean Voronoi diagram of 3D spheres," 16th Canadian Conference on Computational Geometry, 2004, Montreal, Quebec, Aug. 9-11, 2004, pp. 176-179.

Subject: patent related papers and issues.

Deok-Soo Kim, Youngsong Cho, Donguk Kim, "Euclidean Voronoi diagram of 3D spheres by tracing edges," Hanyang University.

Cheol-Hyung Cho, Youngsong Cho, Donguk Kim, Deok-Soo Kim, "Pockets Recognition on Proteins: Euclidean Voronoi Diagram and Convex Hull Based Approach," 2005 CAD/CAM.

Deok-Soo Kim, Donguk Kim, Youngsong Cho, Joonghyun Ryu, Cheol-Hyung Cho, Joon Young Park, and Hyun Chan Lee, "Visualization and analysis of protein structures using Euclidean Voronoi diagram of atoms".

A. Goede, R. Preissner, C. Frömmel, "Voronoi Cell: New Method for Allocation of Space among Atoms: Elimination of Avoidable Errors in Calculation of Atomic Volume and Density," CCC 0192-8651/97/091113-11, vol. 18, No. 9, Journal of Computational Chemistry, pp. 1113-1123.

Deok-Soo Kim, Donguk Kim, Kokichi Sugihara, "Voronoi diagram of a circle set from Voronoi diagram of a point set: I. Topology," Computer Aided Geometric Design 18 (2001) 541-562, www.elsevier.com/locate/comaid.

Deok-Soo Kim, Donguk Kim, Kokichi Sugihara, "Voronoi diagram of a circle set from Voronoi diagram of a point set: II. Geometry," Computer Aided Geometric Design 18 (2001) 563-585, www.elsevier.com/locate/comaid.

Hans-Martin Will, "Computation of Additively Weighted Voronoi Cells for Applications in Molecular Biology," Diss. ETH No. 13188, 1999, pp. 1-161.

Joonghyun Ryu, Rhohun Park, Byunghoon Lee, Youngsong Cho, Donguk Kim, Deok-Soo Kim, "Computing molecular surfaces of a protein: an approach based on a Voronoi diagram and a ball blending," Molecular Surface, 2005 CAD/CAM.

Jonghyun Ryu, Donguk Kim, Youngsong Cho, Rhohun Park and Deok-Soo Kim, "Computation Of Molecular Surface Using Euclidean Voronoi Diagram," Computer-Aided Design & Applications, vol. 2, Nos. 1-4, 2005, pp. xxx-yyy, pp. 1-10.

Deok-Soo Kim, Cheol-Hyung Cho, Youngsong Cho, Chung In Won, and Dounguk Kim, "Pocket recognition on a protein using Euclidean Voronoi diagram of atoms".

Deok-Soo Kim, Yong-Chae Chung, Sangwon Seo, Sang-Pil Kim and Chong Min Kim, "Distributions of BCC, FCC, and HCP structures in A1-Co composite materials," Journal of Ceramic Processing Research, vol. 6, No. 1, pp. 0~00 (2004), pp. 1-5.

Deok-Soo Kim, Yong-Chae Chung, Sangwon Seo, Sang-Pil Kim and Chong Min Kim, "Crystal structure extraction in materials using Euclidean Voronoi diagram and angular distributions among atoms," Journal of Ceramic Processing Research, vol. 6, No. 1, pp. 0~00 (2004), pp. 1-5.

Deok-Soo Kim, Youngsong Cho, Donguk Kim, Sangsoo Kim, Jonghwa Bhak, Sung-Hoon Lee, "Euclidean Voronoi diagram of 3D spheres and applications to protein structure analysis".

Deok-Soo Kim, Youngsong Cho, Donguk Kim, Cheol-Hyung Cho, "Protein structure analysis using Euclidean Voronoi diagram of atoms," pp. 1-5.

Amitabh Varshney, Frederick P. Brooks, Jr., David C. Richardson, William V. Wright, Dinesh Manocha, "Defining, Computing, and Visualizing Molecular Interfaces," Proceedings, IEEE Visualization 95, Oct. 29-Nov. 3, 1995, Atlanta, GA, pp. 36-43.

Borislav Angelov, Jean-Francois Sadoc, Rémi Jullien, Alain Soyer, Jean-Paul Mornon, "Nonatomic Solvent-Driven Voronoi Tessellation of Proteins: An Open Tool to Analyze Protein Folds," Proteins: Structure, Function, and Genetics 49:446-456 (2002).

Alain Soyer, Jacques Chomilier, Jean-Paul Mornon, Rémi Jullien, and Jean-Francois Sadoc, "Voronoï Tessellation Reveals the Condensed Matter Character of Folded Proteins," vol. 85, No. 16, Physical Review Letters, Oct. 16, 2000, pp. 3532-3535.

Anne Poupon, "Voronoi and Voronoi-related tessellations in studies of protein structure and interaction," www.sciencedirecto.com, Current Opinion in Structural Biology 2004, 14:233-241.

Klaus P. Peters, Jana Fauck and Cornelius Frömmel, "The Automatic Search for Ligand Binding Sites in Proteins of Known Three-dimensional Structure Using only Geometric Criteria," J. Mol. Biol. (1996) 256, 201-213.

F. Aurenhammer, "Power Diagrams: Properties, Algorithms And Applications," Siam J. Comput., vol. 16, No. 1, Feb. 1987, pp. 78-96.

Yih-En Andrew Ban, Herbert Edelsbrunner and Johannes Rudolph, "Interface Surfaces for Protein-Protein Complexes," pp. 1-11.

Jean-Daniel Boissonnat, Menelaos I. Karavelas, "On the combinatorial complexity of Euclidean Voronoi cells and convex hulls of $d$-dimensional spheres," pp. 305-312.

Herbert Edelsbrunner, Michael Facello and Jie Liang, "On the Definition and the Construction of Pockets in Macromolecules," Apr. 17, 1998, pp. 1-19.

Marina Gavrilova, "Proximity and Applications in General Metrics," The University of Calgary, May, 1998, pp. 1-250.

\* cited by examiner

US 7,679,615 B2

CALCULATING THREE-DIMENSIONAL (3D) VORONOI DIAGRAMS

CROSS REFERENCE TO RELATED APPLICATIONS

This application claims the benefit of U.S. provisional patent application having Ser. No. 60/567,860 and the title "Euclidean Voronoi Diagram of Spheres", filed on May 4, 2004. This application also claims the benefit of U.S. provisional patent application having Ser. No. 60/568,784 and the title "Euclidean Voronoi Diagram of Spheres", filed on May 6, 2004. Both of these provisional applications are incorporated herein by reference in their entireties.

FIELD OF THE DISCLOSURE

The present disclosure relates generally to geometry and, more particularly, to Voronoi diagrams.

BACKGROUND

Voronoi diagrams have been known as one of the central topics in many disciplines in science and engineering, including computational geometry. Due to its natural descriptive and manipulative capabilities, the Voronoi diagram and its variations have been known by names, such as a Thiessen polygon, a medial axis transformation (MAT), a symmetric axis transformation (SAT), a skeleton, a proximity map, a Dirichlit tessellation, a thinning, and a variety of other names.

Ordinary Voronoi diagrams for point sets (also referred to as "point-set Voronoi diagrams") have been studied extensively, and their properties are well-known to those having skill in the art. Two-dimensional (2D) and higher order analyses have been performed on point-set Voronoi diagrams. These point-set Voronoi diagrams are also referred to herein as VD(P).

One example of a VD(P) is shown in FIG. 1. As shown in FIG. 1, the VD(P) includes a set of points $105a \ldots 105c$ (referred to in the aggregate as 105). Between each pair of points there exists an edge $115a \ldots 115c$ (referred to in the aggregate as 115). Each edge 115 is a perpendicular bisector of a line segment that joins its corresponding points 105. For example, edge 115a is a perpendicular bisector for the line segment that joins points 105a and 105b; edge 115c is the perpendicular bisector for points 105a and 105c; edge 115b is the perpendicular bisector between points 105b and 105c, etc.

As seen in FIG. 1, the VD(P) also has vertices $110a \ldots 110c$ (referred to in the aggregate as 110). These vertices 110 represent a point that is equidistant from three points 105. In that regard, an edge 110 can be seen as disappearing at a vertex 110, or, alternatively, two edges 110 can be seen as coming together to form a vertex 110. As is known, the edges 115 and vertices 110 define polygons $120a \ldots 120c$ (referred to in the aggregate as 120), with each polygon 120 containing its corresponding point 105. In that regard, a polygon 120 is considered the Voronoi region for its corresponding point 105. The network of polygons 120 therefore represents the VD(P).

While not a trivial task, the analysis methods related to VD(P) have been extended in an effort to analyze and characterize Voronoi diagrams of circle sets. Such circle-set Voronoi diagrams are also referred to herein as VD(C).

A more sophisticated approach was developed in which a Euclidean Voronoi diagram of circles was calculated from the circumference of the circles, rather than from the centers of the circles. Such Euclidean Voronoi diagrams for circles are also referred to herein as EVD(C).

One example of a EVD(C) is shown in FIG. 2. As shown in FIG. 2, the EVD(C) includes circles 210 that are defined, in part, by their corresponding centers 205. Rather than simply bisecting the centers of the circles 210, each point on an edge 215 is equidistant from the nearest point on the circumference of its corresponding circles 210. In that regard, each point on the edge 215 has the same Euclidean distance to the nearest point on the circumference of one corresponding circle as it does to the other corresponding circle. The vertices 220 represent the point that has more than two nearest-neighbor circles 210.

For circles of uniform size, the EVD(C) and the VD(P) for the centers of the circles are virtually indistinguishable. However, as shown in FIG. 2, for non-uniform circles 210, the edges 215 of the EVD(C) can be represented by a hyperbolic function. These hyperbolic functions are described in various papers that have been published, in which the topology and geometry of 2D EVD(C) have been analyzed. For example, two articles by Kim et al. have described in detail the computation of EVD(C). Namely, "Voronoi Diagram of a Circle Set from Voronoi Diagram of a Point Set: I. Topology" and "Voronoi Diagram of a Circle Set from Voronoi Diagram of a Point Set: II. Geometry," published in 2001 in Computer Aided Geometric Design, Volume 18, pages 541-562 and 563-585, respectively. Since the calculation of EVD(C) is known in the art, as evidenced by the publications of Kim et al., further discussion of EVD(C) is omitted here.

Others have attempted to extend the methods of analyzing VD(P) and the EVD(C) to calculate three-dimensional (3D) sphere-set Voronoi diagrams. These sphere-set Voronoi diagrams are also referred to herein as EVD(S). For example, Hans-Martin Will, in his 1999 dissertation ("Computation of Additively-Weighted Voronoi Cells for Applications in Molecular Biology," Swiss Federal Institute of Technology, Zurich), explained the mathematics behind EVD(S) in great detail. In his dissertation, Will refers to the EVD(S) as additively-weighted Voronoi cells (AWVC). In addition to providing the detailed mathematics behind his model, Will provided an example algorithm for implementing the computation of AWVC for a single Voronoi region.

In a 1999-paper by Luchnikov et al. ("Voronoi-Delaunay Analysis of Voids in Systems of Nonspherical Particles," Physical Review E, Volume 59, Number 6, June 1999), computations of a single Voronoi region for various 3D models were presented. However, in that approach, Luchnikov presented the idea of using a numerical approach, which is relatively cumbersome and inefficient.

Thus, despite such skill in the art, there is still a lack of appropriate algorithms and stable running codes that can calculate a complete Euclidean Voronoi diagram in 3D. Thus, due to the complexities and intricacies of computing a complete Euclidean Voronoi diagram in 3D, many have instead implemented ordinary VD(P), power diagrams, or alpha-shape algorithms, which are known in the art. A need therefore exists in the art for a more practical solution.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE EMBODIMENTS

Figure 1:
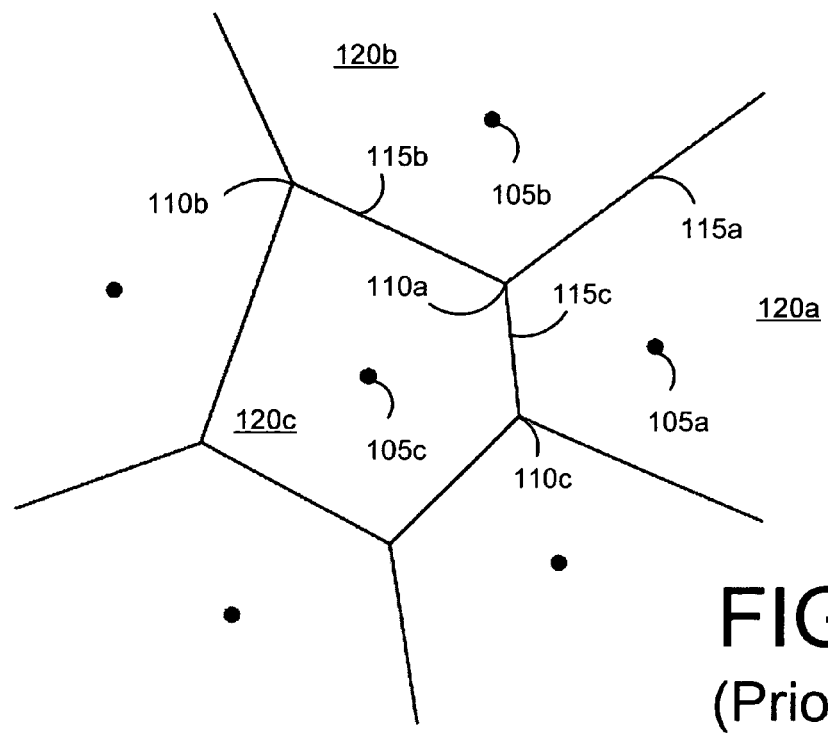
FIG. 1 is a diagram illustrating an ordinary Voronoi diagram of a two-dimensional (2D) point set (VD(P)) from the prior art.
Figure 2:
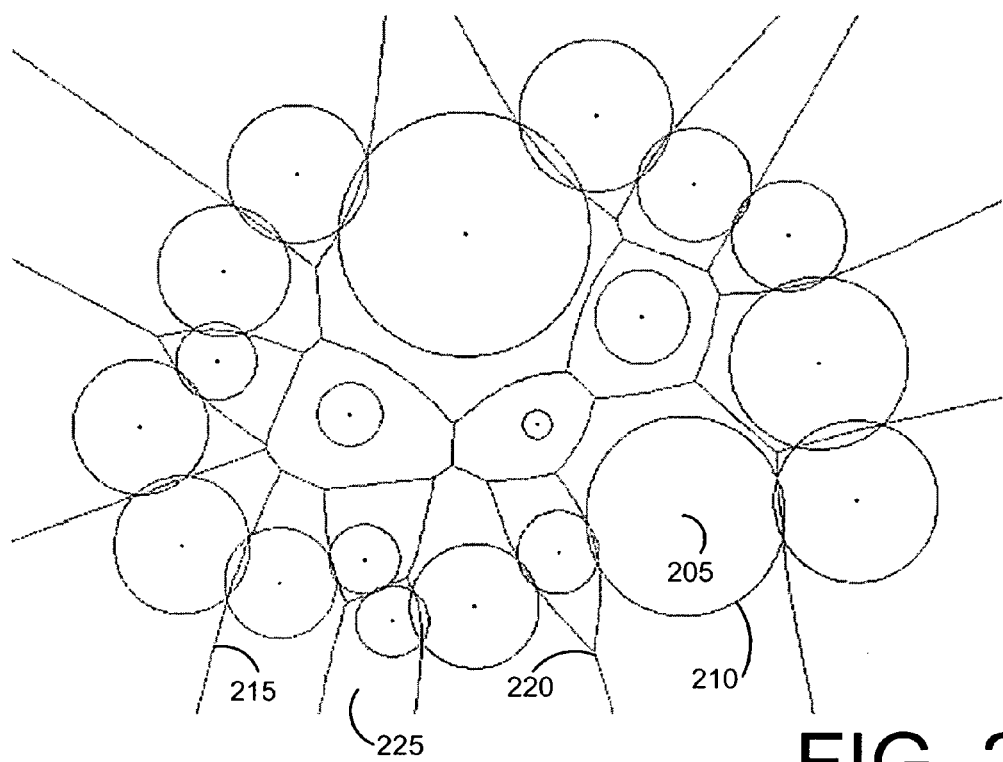
FIG. 2 is a diagram illustrating a 2D Euclidean Voronoi diagram of a circle set (EVD(C)) from the prior art.

Reference is now made in detail to the description of the embodiments as illustrated in the drawings. While several embodiments are described in connection with these drawings, there is no intent to limit the disclosure to the embodiment or embodiments disclosed herein. On the contrary, the intent is to cover all alternatives, modifications, and equivalents.

As noted above, Voronoi diagrams find utility in characterizing various systems, from the biological arena to the arena of materials sciences. While point-set Voronoi diagrams (VD (P)) and circle-set Voronoi diagrams (VD(C)) have previously been studied, there still exists a need for a robust and efficient approach to computing three-dimensional (3D) Voronoi diagrams.

This disclosure provides systems and methods for computing 3D Voronoi diagrams. Specifically, the 3D space comprises 3D objects that are mathematically definable. For example, one such environment includes sphere sets, with each sphere in the set being mathematically defined its center coordinate and radius. These sphere-set Euclidean Voronoi diagrams (EVD(S)) can be used to simulate biological environments (e.g., ribonucleic acids (RNA), deoxyribonucleic acids (DNA), proteins, etc.) or other environments that are known in materials sciences. Other mathematically-definable 3D sets can include sphero-cylinders or cylinders. For illustrative purposes, only the EVD(S) is explained in greater detail below. However, one will appreciate that similar approaches can be used to calculate EVD(X), as long as "X" can be mathematically defined.

For some embodiments, the EVD(S) is computed by accessing a set of 3D objects, and mathematically computing a Voronoi region associated with each 3D object. Each 3D object in the accessed set is mathematically defined. Thus, unlike prior approaches, in which the Voronoi diagram was computed using numerical methods, the disclosed approach computes the complete Voronoi diagram mathematically, thereby improving the efficiency of the computation.

Figure 10A:
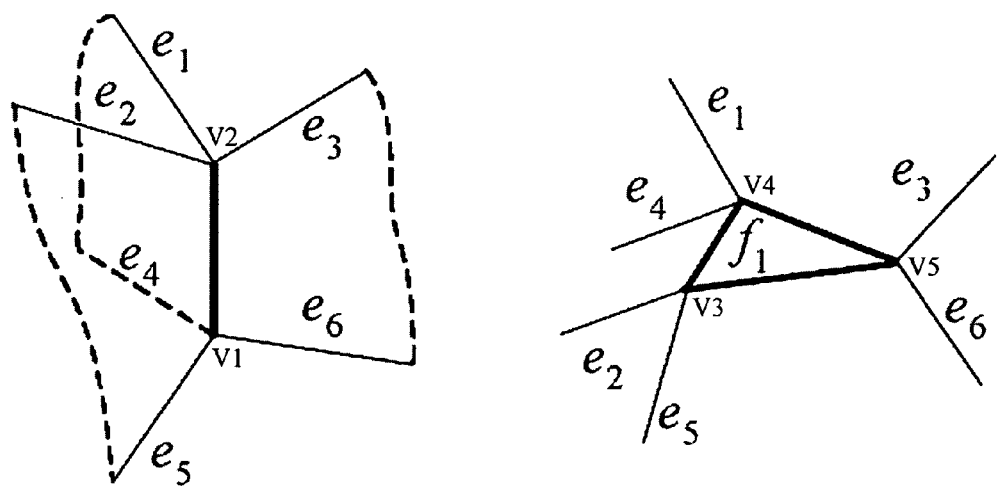
FIGS. 10A through 10D are diagrams illustrating various events associated with the region-expansion algorithm.

The following terms are provided and used consistently throughout this disclosure to facilitate explanation of the EVD(S). However, it should be appreciated that these terms are not limiting to the disclosure, but, rather, only provided for illustrative purposes. Referring to FIG. 10A, if a generator (or a nucleation point) is located below the region defined by e4, e5, and e6, then each face that interfaces with the generator is referred to as a "on face." The region that is bounded by the on faces is referred to as the "Voronoi region of the generator." The edges on the on faces are referred to as "on-edges." Thus, for example, in the particular example of FIG. 10A, the edges e4, e5, and e6 would be considered to be on-edges. In the example of FIG. 10A, the edge defined by V1-V2 will shrink as the Voronoi region of the generator expands. This shrinking edge of FIG. 10A is referred to as a "radiating-edge." All other edges (e.g., e1, e2, and e3 of FIG. 10A) are referred to as "off-edges."

As one can see, each Voronoi face is located at the boundary between two adjacent Voronoi cells. Each Voronoi edge is located at the boundary between two Voronoi faces. Each Voronoi vertex is located at the intersection of at least three Voronoi edges.

Given this, an example data structure comprises Voronoi cells, which includes Voronoi faces that define the Voronoi cell as well as a generator sphere associated with the Voronoi cell. Additionally, the example data structure can include Voronoi faces, which are associated with the corresponding two Voronoi cells on each side of a Voronoi face. The example data structure further comprises edges, each of which are associated with two vertices, three-partial edges (discussed below), and an edge equation. The two vertices define the ends of the edges, and each partial edge points to a corresponding face associated with the edge. The edge equation is a rational quadratic Bézier equation, which is one way to represent a conic curve. The example data structure further comprises vertices, each of which is associated with four (or more) incident edges, a position (e.g., (X,Y,Z) or other known coordinate), and a radius of a tangent sphere.

While an example data structure is provided for illustrative purposes, it should be appreciated by one having skill in the art that various information related to Voronoi cells can be added or removed, depending on the desired performance of the processing algorithm.

Figure 3:
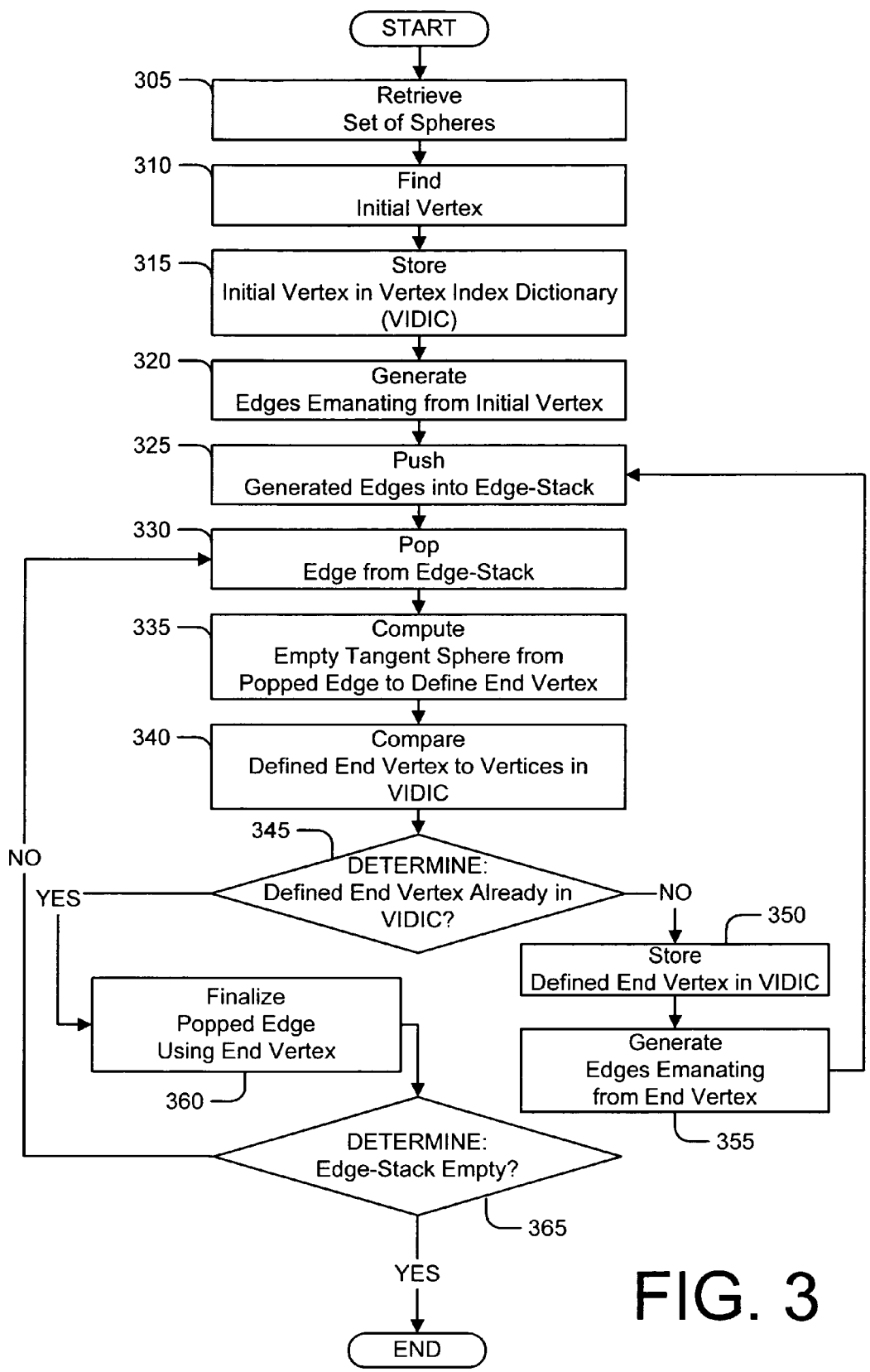
FIG. 3 is a flowchart showing an embodiment of an edge-tracing algorithm for computing a complete three-dimensional (3D) Euclidean Voronoi diagram of a sphere set EVD (S).

FIG. 3 is a flowchart showing an embodiment of an edge-tracing algorithm for computing a complete three-dimensional (3D) Euclidean Voronoi diagram of a sphere set. Such a Euclidean Voronoi diagram for a sphere set is also referred to herein as EVD(S). For a clearer exposition of the edge-tracing algorithm, the following terminology is employed.

Let $B=\{b_1, b_2, \ldots, b_n\}$ be a set of generators where $b_i$ is a 3D spherical ball. Hence, $b_i=(c_i,r_i)$, where $c_i=(x_i,y_i,z_i)$ denotes the Cartesian coordinates for the center of the ball, and $r_i$ denotes the radius of the ball. For some embodiments, it is presumed that no ball is fully contained within another ball. Associated with each ball $b_i$ is a region $VR(b_i)$, which is referred to as the Voronoi region for the ball $b_i$, where $VR(b_i) = \{p | dist(p,c_i)-r_i \leq dist(p,c_j)-r_j, i \neq j\}$. Then $EVD(B)=\{VR(b_1), VR(b_2), \ldots, VR(b_n)\}$ is called the Euclidean Voronoi diagram for set B, with the distance being calculated as the ordinary Euclidean distance.

Similar to ordinary Voronoi diagrams, some Voronoi regions that correspond to balls on the boundary of the convex hull of B are unbounded. Other regions are bounded by a set of boundary faces, which are referred to as Voronoi faces. Each Voronoi face is defined by two neighboring balls and, for sphere-set Voronoi diagrams, each Voronoi face can be represented by a hyperboloid.

One Voronoi face intersects with another Voronoi face to form a Voronoi edge. The intersection of Voronoi edges is referred to as a Voronoi vertex. For some embodiments, the degree of a vertex is presumed to be four. For such embodiments, there is a sphere that is tangent to four balls. This tangent sphere is centered at the vertex, and is empty, meaning that no other ball is intersecting within the empty tangent sphere.

Given four generator balls $b_i$, where i=1, 2, 3, and 4, the tangent spheres can be computed by solving a quadratic equation, where the equation is obtained by an explicit formulation of equidistant points from the four balls. Such a solution can include none, one, or two solutions.

Unless it is a degenerate case, an edge is defined as a locus of points equidistant from the surfaces of three surrounding balls. Thus, the Voronoi edge is the solution of three equations, and it can be shown that the Voronoi edges are planar and, also, are conics. Such conics can be represented mathematically as a rational quadratic Bézier curve, once five parameters are known. These parameters include two end points, tangent vectors at both endpoints, and a point through which the curve passes. For the EVD(S), the two end points are the Voronoi vertices. The tangent vector at a Voronoi vertex is obtained as a vector equiangular with three vectors starting from the vertex and ending at the centers of the three balls that define the edge. The passing point can be found by defining a plane P that passes through the centers of the three balls. The intersection of P with the three balls results in three circles on P, and the passing point on this plane is the center point of a circle that is tangent to these three circles. This is known as Apollonius 10th Problem, and the solution to such a problem is well-known to those of skill in the art.

It should be noted that, when an edge is either circular or elliptical, then a problem may arise. For example, when a smaller ball is located between two larger balls, and the center points of all three balls are collinear, this results in a circular edge. If the center, smaller ball is slightly offset from collinearity (i.e., is non-collinear with the centers of the other two balls), then this results in an elliptical edge. These situations result in two categories, which are referred to herein as edge-connected and edge-disconnected categories. The edge-tracing algorithm can accommodate the edge-connected category. However, for the edge-disconnected category, it is preferential to construct an edge graph for the larger balls first, and then another edge graph for the smaller balls.

A Voronoi face interposes two topologically neighboring balls $b_i$ and $b_j$, such that $|p-c_i|-r_i=|p-c_j|-r_j$. Hence, a Voronoi face is a hyperboloid and implicit equation can be mathematically calculated. The principal uses of Voronoi faces are the computations of volumes and boundary areas of Voronoi regions. Additionally, Voronoi faces can be employed to enhance visualization of the geometry and topology of 3D structures.

For some embodiments, it is easier to perform a coordinate transformation in order to simplify the computation of the Voronoi face. For example, by transforming two balls such that the larger ball is located at the origin and the smaller ball is located on the positive Z-axis, the Voronoi face between the two balls becomes a single-valued function with reference to the X-axis and the Y-axis. Similarly, the boundaries of the faces, which are rational quadratic Bézier functions, can also be similarly transformed. Since coordinate transformations are known to those having skill in the art, discussions of such coordinate transformations is omitted here.

Given that Voronoi diagrams can be defined by the Voronoi vertices, the Voronoi edges, and the Voronoi faces, such Voronoi diagrams can be computed using an edge-tracing algorithm, such as that shown with reference to FIG. 3. As shown in FIG. 3, some embodiments of the process begin by retrieving (305) a set of spheres. The set of spheres, for some embodiments, can represent the atoms on proteins, DNA, RNA, or a variety of other molecules. For other embodiments, the set of spheres can represent nucleation points for crystal growth.

The EVD(S) can also be used to analyze the interface between layers of thin films, such as, for example, in semiconductor research. For such applications, when atoms are deposited onto a substrate, the EVD(S) can provide information on their interactions for various deposited layers.

Yet other applications include crystal structure analysis using model data from computer simulations, such as, for example, molecular dynamic simulations or ab initio simulations. For other embodiments, the EVD(S) can also be used for analyzing phenomena at grain boundaries. In fact, as one can imagine, the EVD(S) can be used for almost any geometric study among particles.

Upon retrieving (305) the set of spheres, the process continues by finding (310) an initial vertex. The initial vertex is then stored (315) in a vertex index dictionary (VIDIC). For some embodiments, the VIDIC is simply a database that catalogs vertices of the EVD(S), which will eventually be fully computed by the end of the process in FIG. 3.

Once the initial vertex is found (310) and stored (315) in VIDIC, the process generates (320) edges that emanate from the initial vertex. These edges can be represented as rational quadratic Bézier curves (or other conic curves) for some embodiments. Since Bézier curves are known in the art, further discussion of such curves is omitted here. The generated edges are then pushed (325) into an edge-stack. For other embodiments, the edge equation need not be computed. Thus, for those embodiments, the equations for the edges and faces are computed only when necessary. As is known, this computation can easily be done once the topology of the EVD(S) is obtained.

One edge is popped (330) from the edge-stack, and an empty tangent sphere is computed (335) from the popped edge, thereby defining an end vertex associated with the popped edge. The defined end vertex is compared (340) to the vertices in VIDIC, and the process determines (345) whether the defined end vertex is already in VIDIC. It should be appreciated that several empty tangent spheres can be computed for a popped edge. For those situations, in some embodiments, the tangent sphere that is closest in angular distance to the start vertex of the popped edge is chosen. The angular distance is measured from the start vertex to the center of the empty tangent sphere.

If the defined end vertex is not found in VIDIC, then the process stores (350) that defined end vertex in VIDIC, and generates (355) more edges that emanate from the defined end vertex. The newly-generated edges are then pushed (325) into the edge-stack and queued for subsequent processing. The process then repeats by popping (330) the next edge from the edge-stack.

If, however, the defined end vertex is already in VIDIC, then the process finalizes (360) the popped edge using the previously defined end vertex. In other words, if the end vertex already exists in VIDIC, then the process makes the popped edge complete by making the vertex in VIDIC be the end vertex of the edge. Upon finalizing (360) the popped edge, the process further determines (365) whether or not the edge-stack is empty. If the edge-stack is empty, then the process ends. If, however, the edge-stack is not empty, then the process pops (330) another edge from the edge-stack, and the process repeats until the edge-stack is empty.

When the edge-stack is empty, then all of the edges have been computed, thereby completing the EVD(S). The faces of each Voronoi region can be reconstructed as hyperboloids with edges that are rational quadratic Bézier curves. For other embodiments, the faces need not be computed.

FIGS. 4A through 4G is a flowchart showing an embodiment of a region-expansion algorithm for computing a complete EVD(S). While a specific region-expansion algorithm for a sphere set is shown in FIGS. 4A through 4G, it should be appreciated that such an algorithm can be extended to any 3D surface, so long as the components of the tessellation are mathematically definable.

Employing the nomenclature used in FIG. 3, $b_i$ is also referred to as a generator for $VR(b_i)$. Given a generator, which will eventually expand to its full size starting from a point at its center at a particular time, the generator is referred to as an expanding generator. The corresponding Voronoi region that is being expanded is referred to as an expanding region. As noted above, the Voronoi vertices on the boundary of an expanding region are referred to as on-vertices; the Voronoi edges on the expanding region are referred to as on-edges; and the Voronoi faces on the expanding region are referred to as on-faces. The Voronoi vertices that are not on the expanding region are referred to as off-vertices; the Voronoi edges that have no on-vertices are referred to as off-edges; and the Voronoi faces that have no on-edges are referred to as off-faces. Voronoi edges with an on-vertex and an off-vertex are referred to as radiating edges. In addition, Voronoi edges with on-vertices at both Voronoi vertices are also referred to as radiating edges, if the edge itself is not an on-edge. Faces that have an on-edge and one or more radiating edges are referred to as radiating faces. A vertex sphere is a sphere that is tangent to the generators that define a Voronoi vertex. Thus, the center of a vertex sphere is the vertex itself.

When an ordinary Voronoi diagram for the centers of spheres is used as a beginning, then each Voronoi region can be represented as a polyhedron, which is not necessarily the correct Voronoi region for sphere-set tessellations. From this beginning, when each sphere is grown (or expanded), the corresponding region expands correspondingly. If the topology and the geometry can be maintained between the vertices, edges, faces, and regions, then the complete Voronoi diagram can be computed by repeating the process, generator-by-generator, until the Voronoi regions for all generators are computed. Such a process is referred to herein as a region-expansion process or a region-expansion algorithm.

As an expanding generator increases in its size, the volume of the expanding region correspondingly increases in size. Thus, each on-vertex moves away from the initial expanding region by following the radiating-edge associated with the vertex during region expansion. Similarly, each on-edge moves away from the initial expanding region by following the corresponding radiating face. For sufficiently small expansions in the expanding generator, the combinatorial structure of the diagram remains unchanged. However, for such small expansions, the geometries of the vertices, edges, and faces that are related to the region boundary may be altered.

During the expansion process, topological structural changes can occur if there is sufficient expansion. For example, when an on-vertex moves along a radiating-edge, it may meet a corresponding off-vertex on the radiating-edge. At that point, the radiating-edge shrinks and degenerates to point, which thereafter disappears. Such a change in the combinatorial structure is referred to herein as an event. Various events related to the region-expansion process are discussed with reference to FIGS. 10A through 10D.

Since Voronoi regions are star-shaped, intersections between faces do not occur interior to the face, but at the boundaries of faces. Hence, topological changes can be, in the expansion process, detected by considering the vertices and edges only, for some embodiments. Furthermore, since on-vertices and on-edges are constrained to move along radiating-edges and radiating faces, respectively, the edges on the radiating faces can sufficiently characterize the expansion. Since events denote changes in topology due to moving on-vertices or on-edges, the next event occurs at edges on the radiating-faces during region expansion. However, every edge except on-edges can be associated with an event if the size of the expanding generator is sufficiently large. Since generator spheres have prescribed sizes, typically only a subset of events can be realized. It is also worthwhile to note that on-vertices and on-edges do not have any associated states.

Figure 4A:
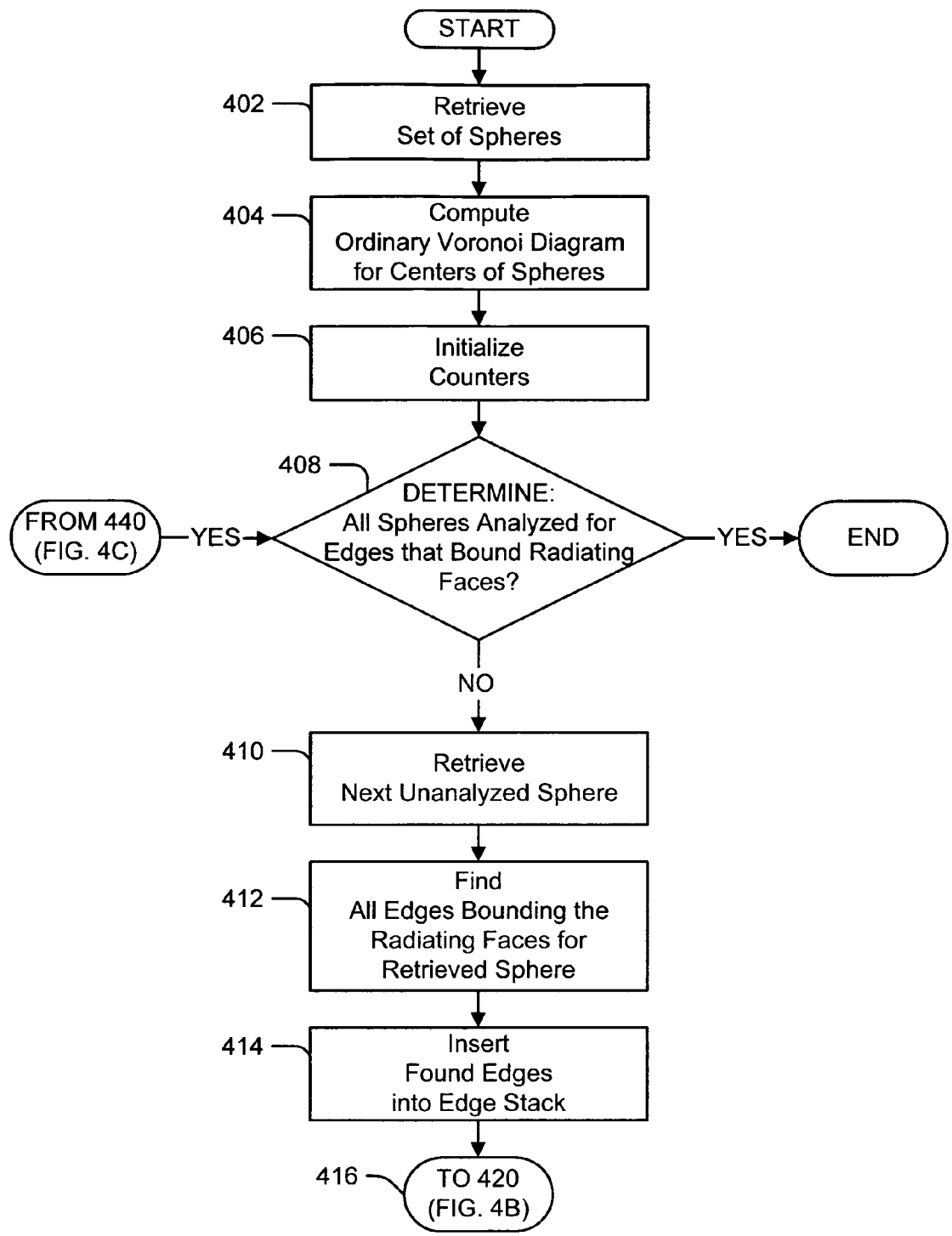
FIGS. 4A through 4G are flowcharts showing an embodiment of a region-expansion algorithm for computing a complete 3D EVD(S).

Given such an overview of region-expansion, an embodiment of a region-expansion algorithm is provided with reference to FIGS. 4A through 4G. As shown in FIG. 4A, the region-expansion embodiment begins by retrieving (402) a set of spheres. Upon retrieving (402) the sphere set, an ordinary Voronoi diagram is computed (404) using the centers of the retrieved spheres. Since the computation of point-set Voronoi diagrams are known in the art, a description of the process for computing (404) the ordinary Voronoi diagram is omitted here. Since the final EVD(S) will be computed for each point in the tessellation, the algorithm then initializes (406) all of the counters that reflect the number of points in the tessellation.

For some embodiments, rather than computing the EVD(S) on the raw sphere-set data, all of the spheres are shrunk so that the smallest sphere in the sphere set reduces to a point. In other words, the radius of the smallest sphere within the set is determined and, thereafter, that radius is subtracted from all of the spheres in the sphere set. By reducing the radius of all of the spheres by the radius of the smallest sphere in the set, the computation is simplified.

Upon initialization (406) of the counters, the algorithm determines (408) whether or not all of the spheres in the retrieved set have been analyzed for edges that bound their respective radiating faces. In other words, for some embodiments, the algorithm determines whether or not all of the spheres have gone through a sphere-expansion process (as described herein) and, also, whether or not the necessary computations resulting from the sphere-expansion process have been performed. If all of the spheres have been analyzed, then this indicates that the EVD(S) has been completely computed for the retrieved sphere set. Hence, if all of the spheres have been analyzed, then the process ends. However, if all of the spheres have not been analyzed, then the algorithm retrieves (410) the next unanalyzed sphere.

Upon retrieving (410) the next unanalyzed sphere, the algorithm finds (412) all of the edges that bound the radiating faces of the retrieved sphere. The found edges are then inserted (414) into an edge-stack. The process continues (416) to FIG. 4B.

Figure 4B:
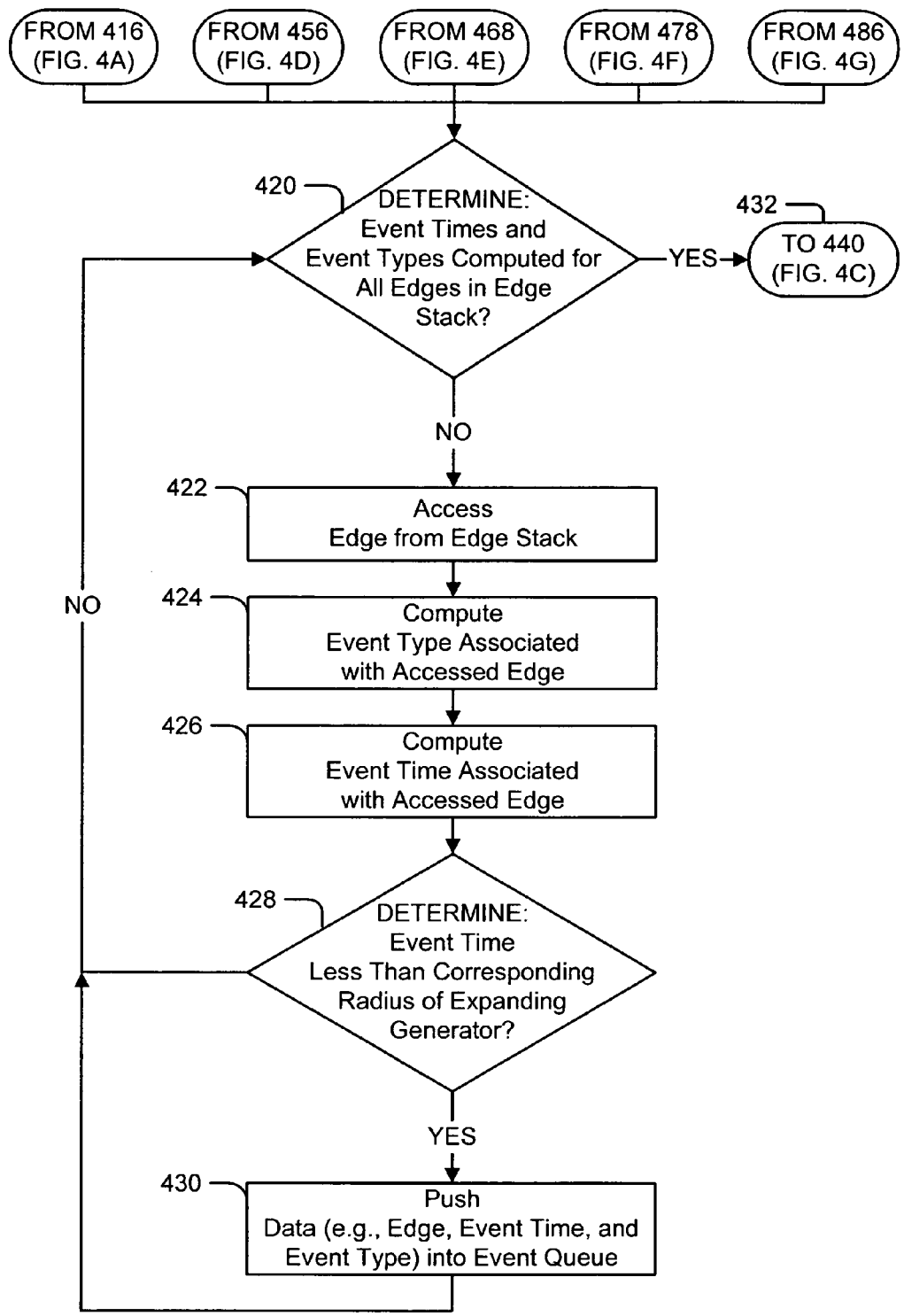

As shown in FIG. 4B, the algorithm next determines (420) whether or not the event times and event types have been computed for all of the edges in the edge stack. In other words, the algorithm checks to see if an exit condition for the loop has been met. If the event times and event types have not been computed for all of the edges in the edge stack, then the algorithm accesses (422) one edge from the edge-stack. Thereafter, the algorithm computes (424) the event type associated with the accessed edge, and also computes (426) the event time associated with the accessed edge. The event type and event time are discussed in greater detail with reference to FIGS. 10A through 10D below.

Upon computing (424, 426) both the event type and the event time of an edge, the algorithm next determines (428) whether or not the event time of the edge is less than the corresponding radius of the expanding generator. An event time is the radius of the expanding generator when the event occurs. If the event time of the edge is not less than the corresponding radius of the expanding generator, then the process loops back and again determines (420) whether or not the event types and event times for all of the edges in the edge-stack have been computed. If, on the other hand, the even time of the edge is less than the corresponding radius of the expanding generator, then the algorithm pushes (430) data into an event queue. The data can include information related to the edge, such as event type, event time, and other relevant information. The event queue is a priority queue that uses the event time as a key. Upon pushing (430) the data into the event queue, the process loops back and again determines (420) whether or not the even types and event times for all of the edges in the edge-stack have been computed. Upon determining that the event types and event times have been computed for all edges in the edge-stack, the process continues (432) to FIG. 4C.

Figure 4C:
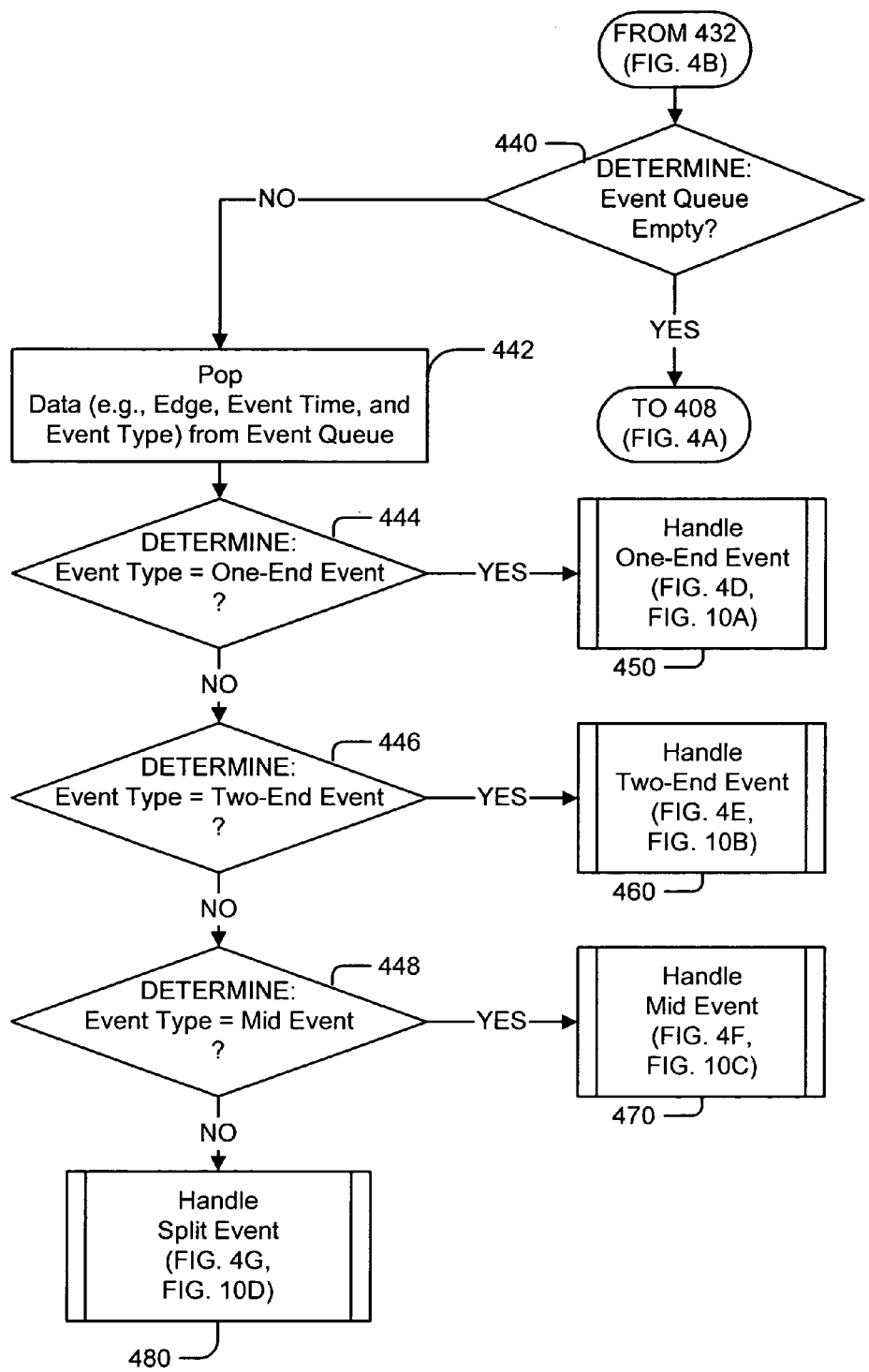
Figure 4D:
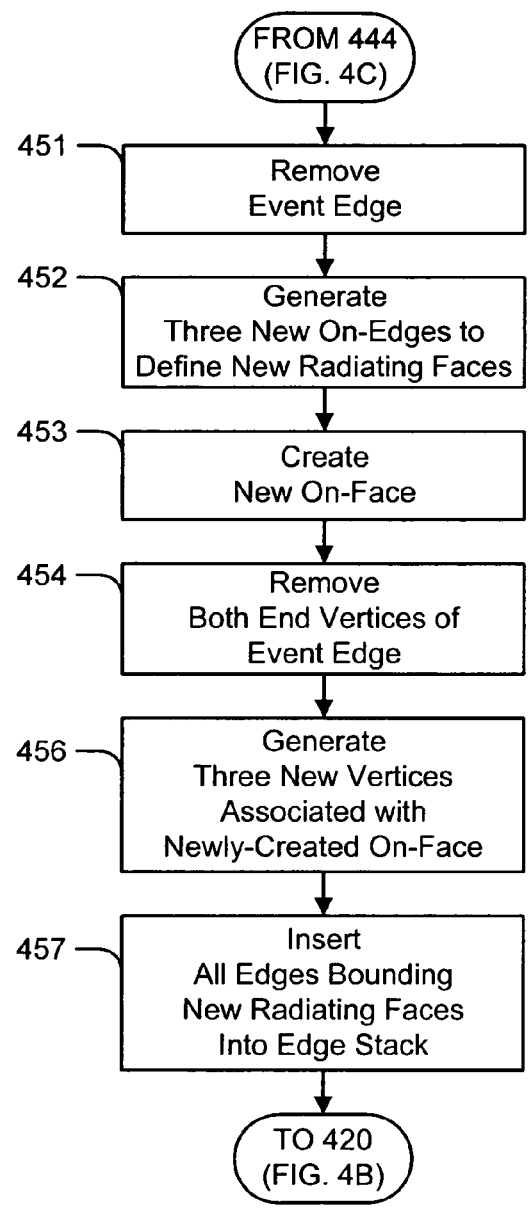
Figure 4E:
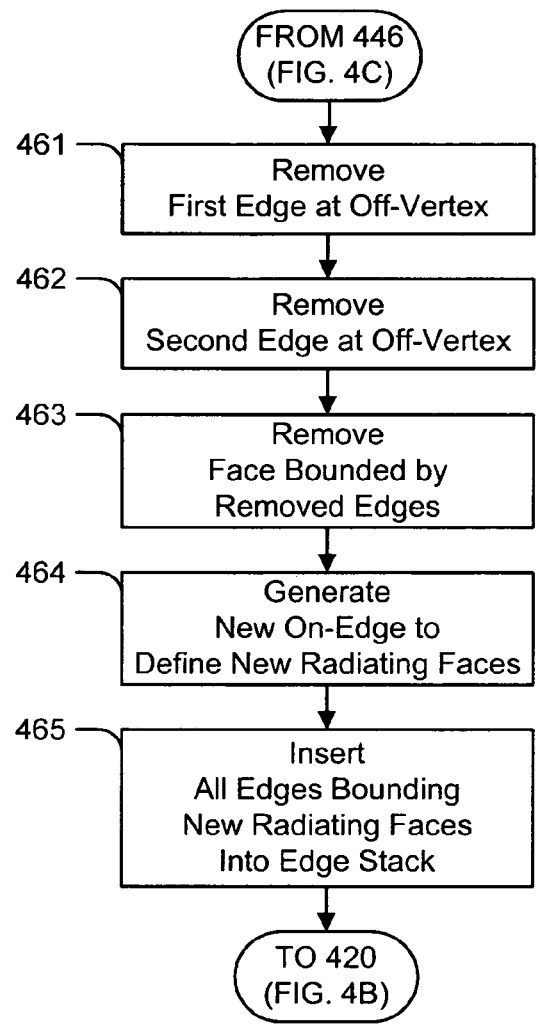
Figure 4F:
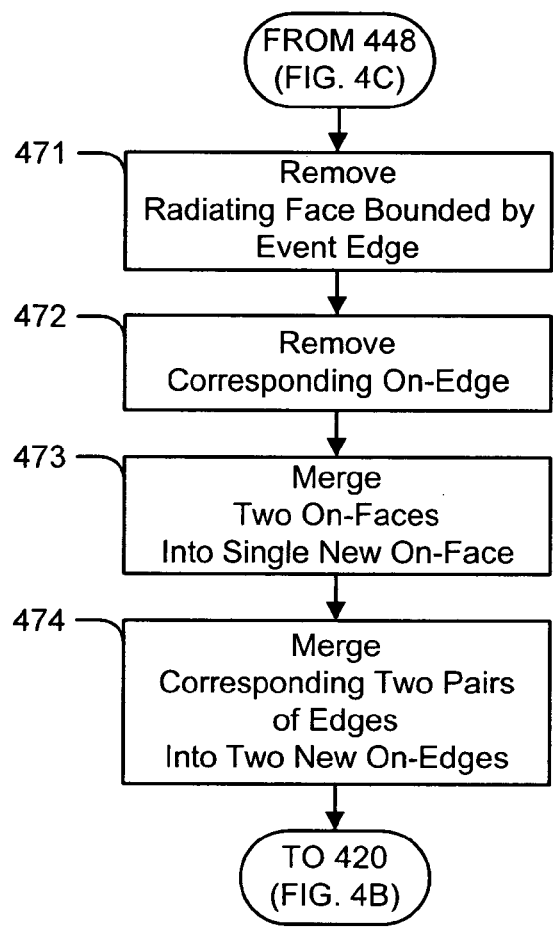
Figure 4G:
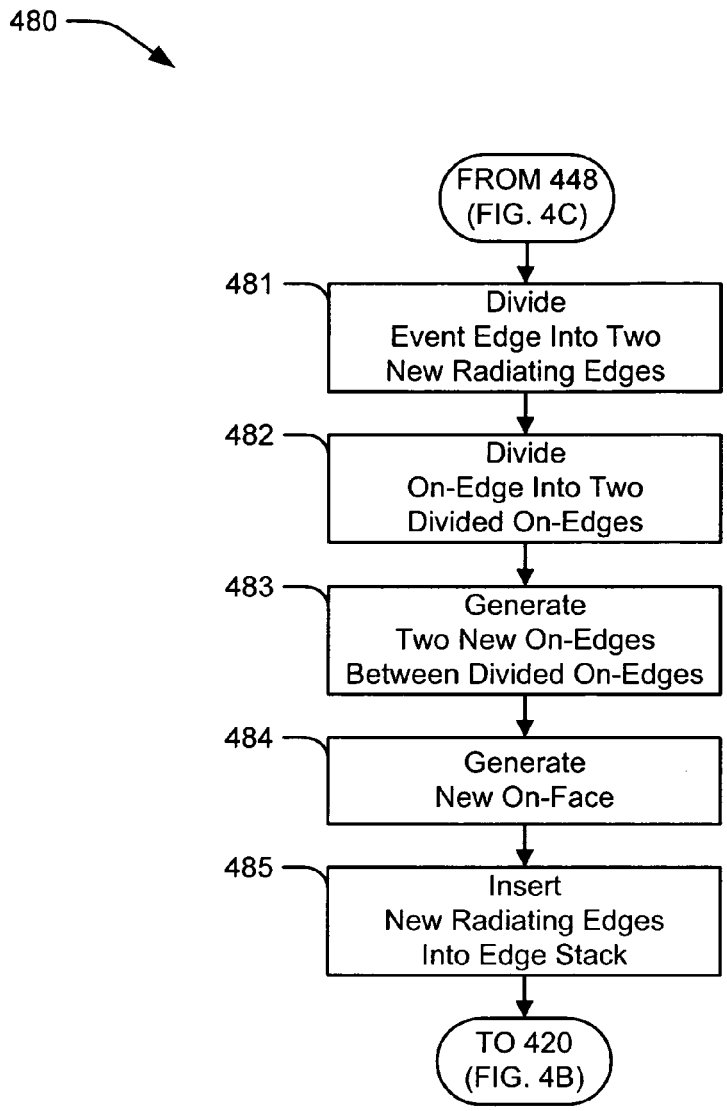

As shown in FIG. 4C, once all of the event times and event types have been computed, the algorithm next determines (440) whether or not the event queue is empty. If the event queue is empty, then the process returns to FIG. 4A, and the algorithm again determines (408) whether or not all spheres have been analyzed for edges that bound the radiating faces of their respective spheres. If, however, the event queue is not empty, then the algorithm pops (442) the next available immediate event that has a lower value of event time from the event queue.

Using the popped data, the algorithm determines (444) whether or not the event type is a one-end event. If the algorithm determines (444) that the event type is a one-end event, then the process continues (450) to a subroutine that handles a one-end event. An embodiment of the one-end event subroutine (450) is described in greater detail with reference to FIGS. 4D and 10A.

Alternatively, if the event type is not a one-end event, then the algorithm further determines (446) whether or not the event type is a two-end event. If the algorithm determines (446) that the event type is a two-end event, then the process continues (460) to a subroutine that handles a two-end event. An embodiment of the two-end event subroutine (460) is described in greater detail with reference to FIGS. 4E and 10B.

If the event type is also not a two-end event, then the algorithm further determines (448) whether or not the event type is a mid-event. If the algorithm determines (448) that the event type is a mid-event, then the process continues (470) to a subroutine that handles a mid-event. An embodiment of the mid-event subroutine (470) is described in greater detail with reference to FIGS. 4F and 10C.

Finally, if the event type is also not a mid-event, then the process continues (480) to a subroutine that handles a split event. An embodiment of the split-event subroutine (480) is described in greater detail with reference to FIGS. 4G and 10D.

As noted above, FIG. 4D is a flowchart of a one-end event subroutine (450). A one-end event is illustrated with reference to FIG. 10A. In FIG. 10A, if edges e4, e5, and e6 are considered as on-edges and e1, e2, and e3 are considered as off-edges, then vertex V1 moves toward vertex V2, thereby making the edge between V1 and V2 a radiating-edge. As shown in FIG. 10A, when the one-end event triggers, V1 collapses with V2, and the edges e1, e2, e3, e4, e5, and e6 converge at a single point. After the event, a new on-face f1 is born and, consequently, three new on-edges and three new on-vertices, which define f1, are born.

Thus, the one-end event subroutine (450) can be seen as including the steps of removing (451) the relevant event edge, generating (452) three new on-edges that define a new on-face, and creating (453) the new on-face. Correspondingly, the one-end event subroutine (450) also includes removing (454) both end vertices of the event edge, generating (455) three new vertices (V3, V4, and V5) associated with the newly-created on-face, and inserting (457) all edges that bound the new radiating faces into the edge stack. Upon inserting (457) the edges into the edge stack, the subroutine exits to FIG. 4B, in which the algorithm again determines (420) whether or not the event times and event types for all edges in the edge stack have been computed.

Figure 10B:
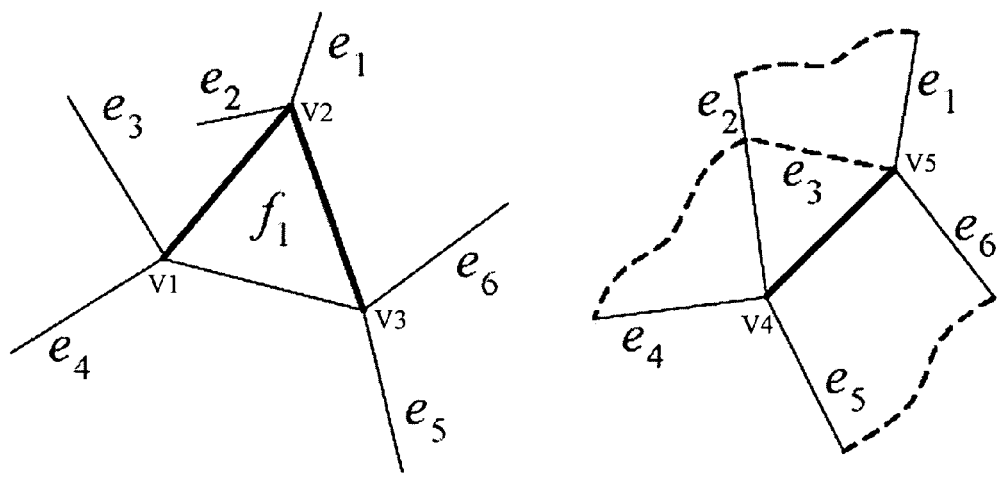

As noted above, FIG. 4E is a flowchart of a two-end event subroutine (460). A two-end event is illustrated with reference to FIG. 10B. In FIG. 10B, consider that edges e1, e3, and e6 extend out of the page while edges e2, e4, and e5 extend into the page. If V1 and V3 are on-vertices, then these two vertices move toward V2 and, when the two-end event triggers, both V1 and V3 collapse with V2. At that point, all edges e1, e2, e3, e4, e5, and e6 converge at a single point. After the event, the two radiating-edges (defined by V1–V2 and V2–V3) disappear simultaneously. Consequently, the face f1 also disappears and a new edge (defined by V4–V5) appears. Edges e1, e3, and e6, which extended out of the page, converge at vertex V5, while edges e2, e4, and e5, which extended into the page, converge at vertex V4.

Thus, the two-end event subroutine (460) can be seen as including the steps of removing (461) the first edge at the off-vertex, removing (462a) the second edge at the off-vertex, removing (462b) the third edge at the off-vertex, and removing (463) the face f1 bounded by the removed edges. Correspondingly, the two-end event subroutine (460) also includes the steps of generating (464) a new on-edge to define new radiating faces, and inserting (465) the edges that bound the new radiating faces into the edge stack. Upon inserting (465) the new edges into the edge stack, the subroutine exits to FIG. 4B, in which the algorithm again determines (420) whether or not the event times and event types for all edges in the edge stack have been computed.

Figure 10C:
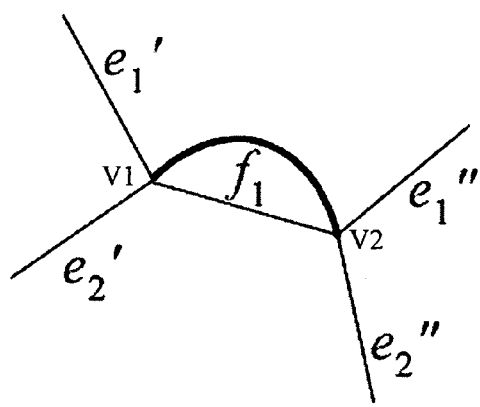
Figure 10C:
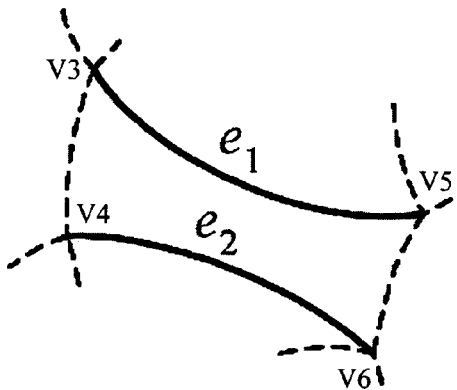
Figure 10D:
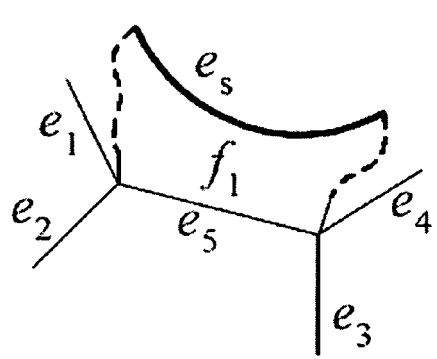
Figure 10D:
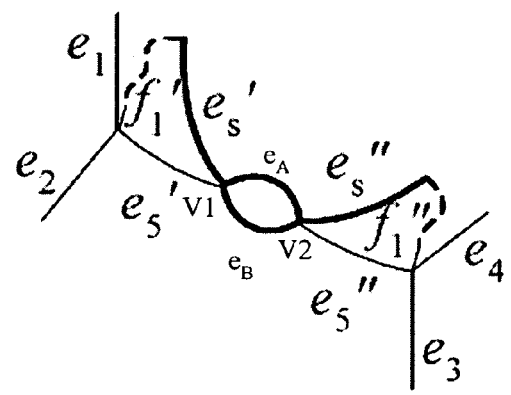

As noted above, FIG. 4F is a flowchart of a mid-event subroutine (470). A mid-event is illustrated with reference to FIG. 10C. As shown in FIG. 10C, during a mid-event, vertices V1 and V2 converge. Thus, when the mid-event triggers, vertices V1 and V2 collapse into a single vertex, and face f1 disappears. At the event time, edges e1', e1'', e2', and e2'' converge to a single point. After the event, the two edges e1' and e1'' evolve to a single edge e1, and the two edges e2' and e2'' evolve into a single edge e2. Thus, the two on-faces collapse into a single on-face.

Thus, the mid-event subroutine (470) can be seen as including the steps of removing (471) a radiating face that is bounded by an event edge, and removing (472) the corresponding on-edge. Consequently, the mid-event subroutine (470) also includes the steps of merging (473) two on-faces into a single new on-face, and merging (474) the corresponding pairs of edges into two new on-edges. Since no new radiating-edges are born in a mid-event, no additional information is added to the edge stack. Thus, at the completion of the mid-event subroutine (470), the subroutine exits to FIG. 4B, and the algorithm again determines (420) whether or not all event times and event types have been computed for the edges in the edge stack.

The edge-graph of EVD(S) may be disconnected for some special cases, such as a small sphere in between two large spheres. This case can be also handled by an extension of a mid-event. When a mid-event occurs, if the face bounded by e1' and e2' and the face bounded by e1" and e2" are from an identical face, then the edge graph is disconnected. Hence, this can be detected by either checking whether both faces are identical or not, or, alternatively, by checking whether the edge-loop formed by e1', e1", e2', and so on, is connected or not.

As noted above, FIG. 4G is a flowchart of a split event subroutine (480). A split event is illustrated with reference to FIG. 10D. In a split event, the event edge does not disappear but, rather, is split into two edges. Each divided edge is considered a new edge to be tested for event type and event time. Thus, at the trigger of a split event, eS converges with e5 at a single point. After the event, face f1 is divided into two separate faces f1' and f1". Similarly, the edge eS is divided into edges eS' and eS", while the edge e5 is divided into edges e5' and e5". Consequently, two new edges eA and eB are born to define a new face.

Given this, the split event subroutine (480) can be seen as including the steps of dividing (481) an event edge into two new radiating-edges, and dividing (482) an on-edge into two divided on-edges. Consequently, the split event subroutine (480) also includes the steps of generating (483) two new on-edges between the divided on-edges, and generating (484) a new on-face. The new radiating-edges are then inserted (485) into the edge stack, and the subroutine exits to FIG. 4B, in which the algorithm again determines (420) whether or not the event times and event types for all of the edges in the edge-stack have been computed.

It should be appreciated that a mathematical approach, similar to that described above, is more robust and efficient than numerical approaches that have been suggested by others in the past.

Various examples of Voronoi diagrams, which resulted from the above-described processes, is shown with reference to FIGS. 5 through 9.

Figure 5:
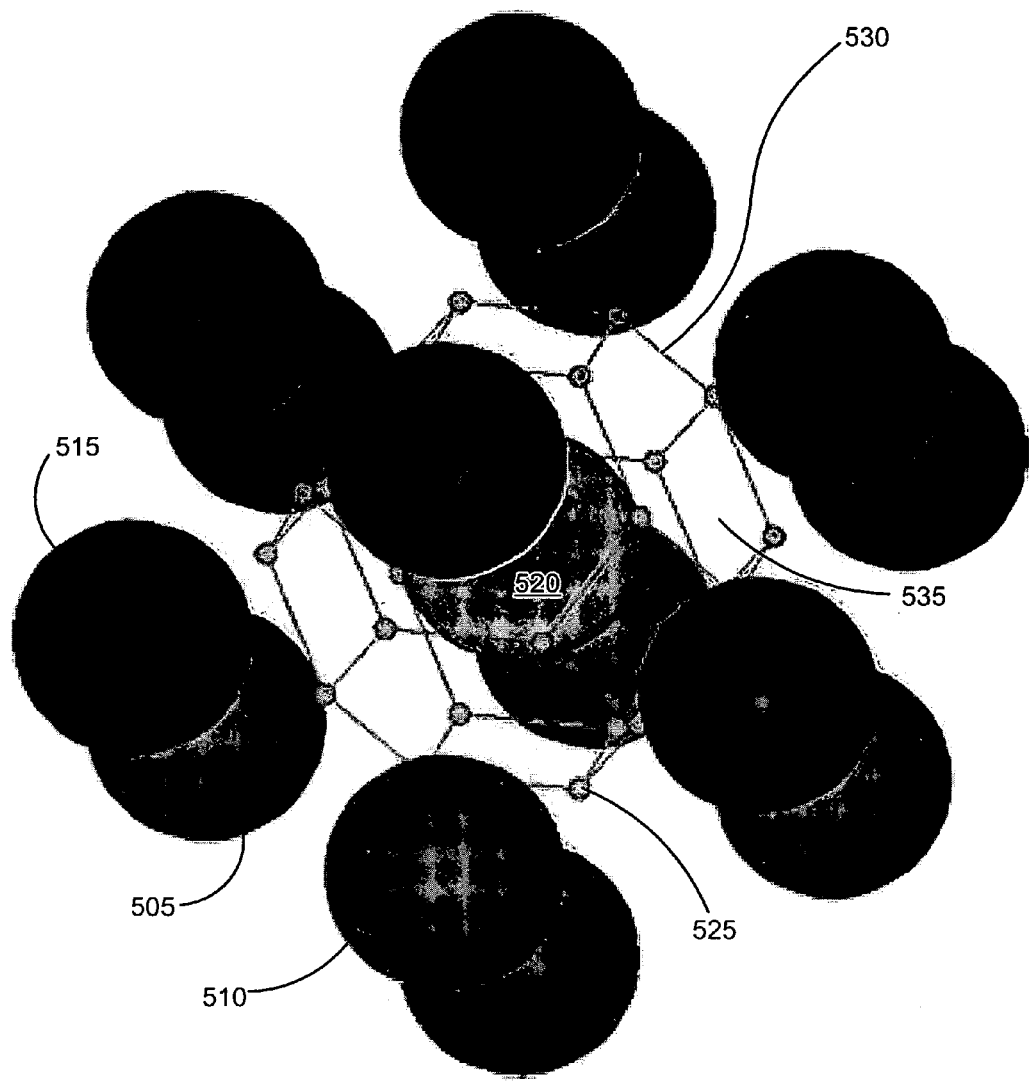
FIG. 5 is a diagram showing one result from a computation of a EVD(S) for a set of spheres having fifteen uniform spheres.

FIG. 5 is a diagram showing one result from a computation of a EVD(S) for a set of spheres having fifteen uniform spheres. The EVD(S) of FIG. 5 can be computed using either the edge-tracing algorithm of FIG. 3 or the region expansion algorithm of FIGS. 4A through 4G.

As shown in FIG. 5, when each of the spheres 505, 510, 515, 520 are identical in size, the resulting Voronoi diagram is polyhedral in shape. Thus, the Voronoi surfaces 535 degenerate into a special hyperboloid case of a plane. The Voronoi faces 535, vertices 525, and edges 530 are shown in FIG. 5. For ease of visualization, the edges that extend to infinity are omitted in FIG. 5.

Figure 6:
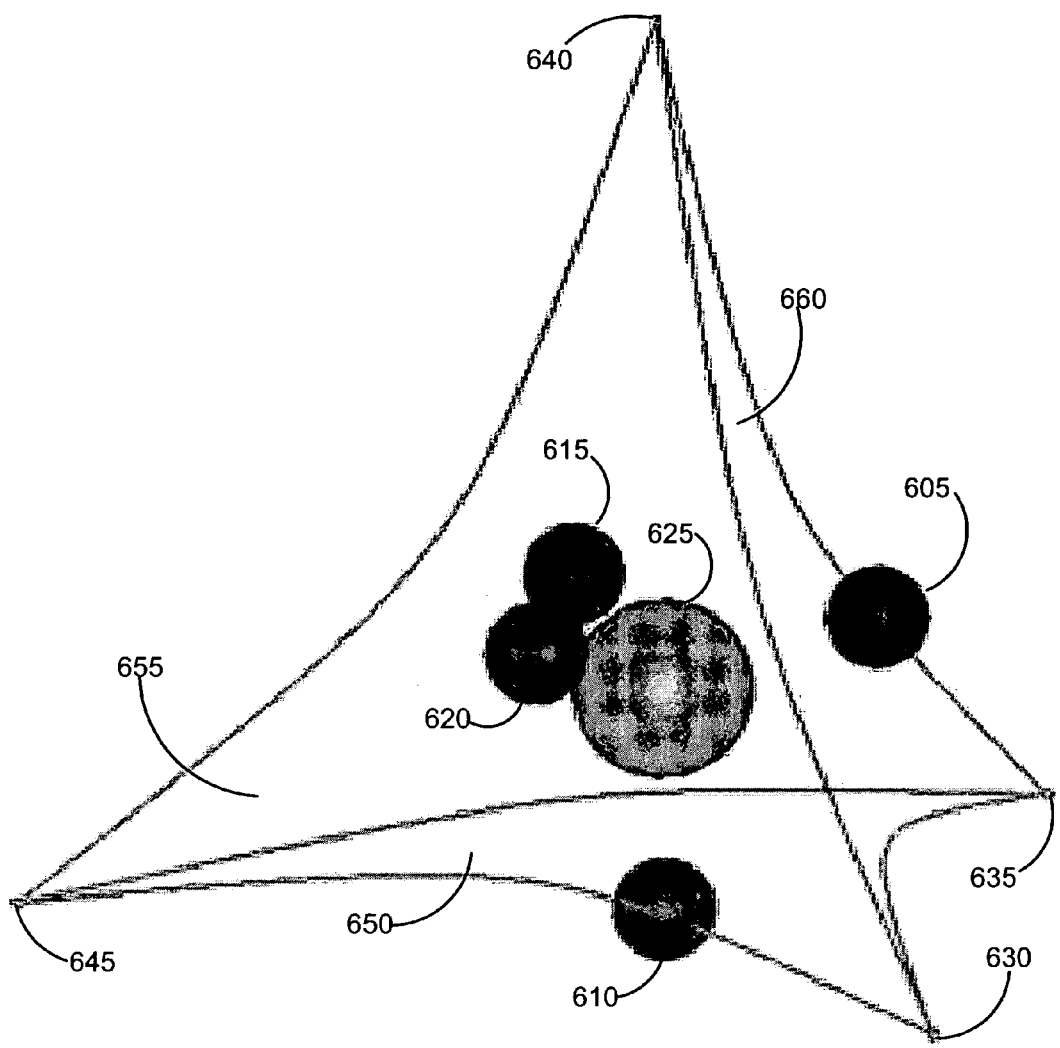
FIG. 6 is a diagram showing another result from a computation of a EVD(S) for a set of spheres having five non-uniform spheres.

FIG. 6 is a diagram showing another result from a computation of a EVD(S) for a set having five non-uniform spheres. The EVD(S) of FIG. 6 can be computed using either the edge-tracing algorithm of FIG. 3 or the region expansion algorithm of FIGS. 4A through 4G.

As shown in FIG. 6, a central sphere 625 is surrounded by four peripheral spheres 605, 610, 615, 620, which are arranged in a tetrahedral arrangement. For ease of visualization, the four peripheral spheres 605, 610, 615, 620 are uniform in size, while the central sphere 625 is significantly larger in size. As seen here, a Voronoi face 650 is interposed between the central sphere 625 and one of the peripheral spheres 610. Three other Voronoi faces are readily apparent in FIG. 6. Each of the Voronoi faces is hyperboloid, and the edges of each Voronoi face is a conic and can be represented mathematically by, for example, a rational quadratic Bézier equation, if necessary. For example, the front face 655 is defined by three vertices 645, 640, 630, and these three vertices further define three edges. For convenience, the edges that extend to infinity are omitted in FIG. 6.

Figure 7:
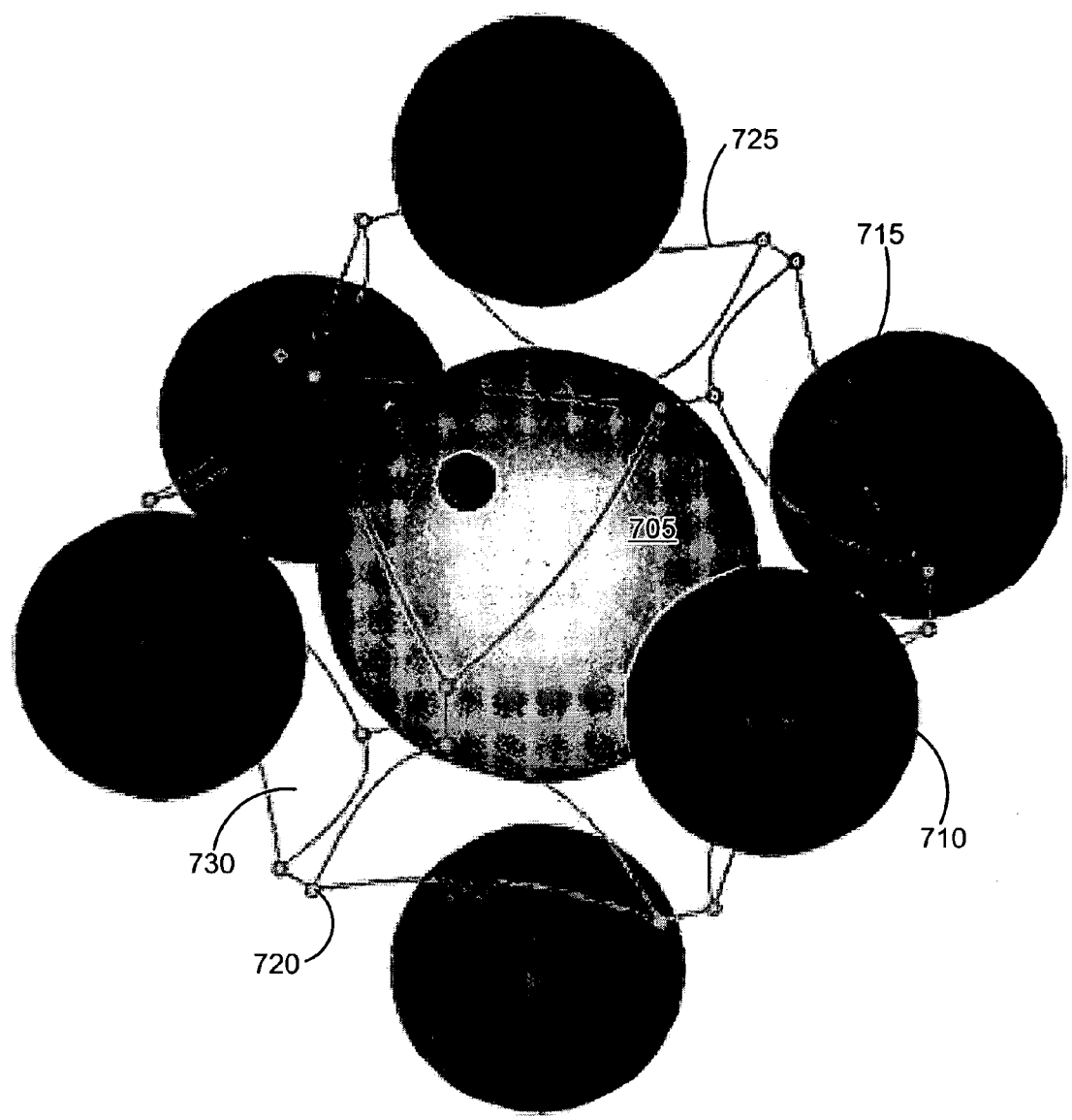
FIG. 7 is a diagram showing another result from a computation of a EVD(S) for a set of spheres having fifteen non-uniform spheres.

FIG. 7 is a diagram showing another result from a computation of a EVD(S) for a set of spheres having fifteen non-uniform spheres. The EVD(S) of FIG. 7 can be computed using either the edge-tracing algorithm of FIG. 3 or the region expansion algorithm of FIGS. 4A through 4G. Unlike the diagram of FIG. 5, the Voronoi diagram exhibits non-planar faces for FIG. 7. The reason being that the hyperboloid faces manifest themselves more clearly due to the non-uniformity of the spheres. For convenience, the edges that extend to infinity are omitted in FIG. 7.

Figure 8:
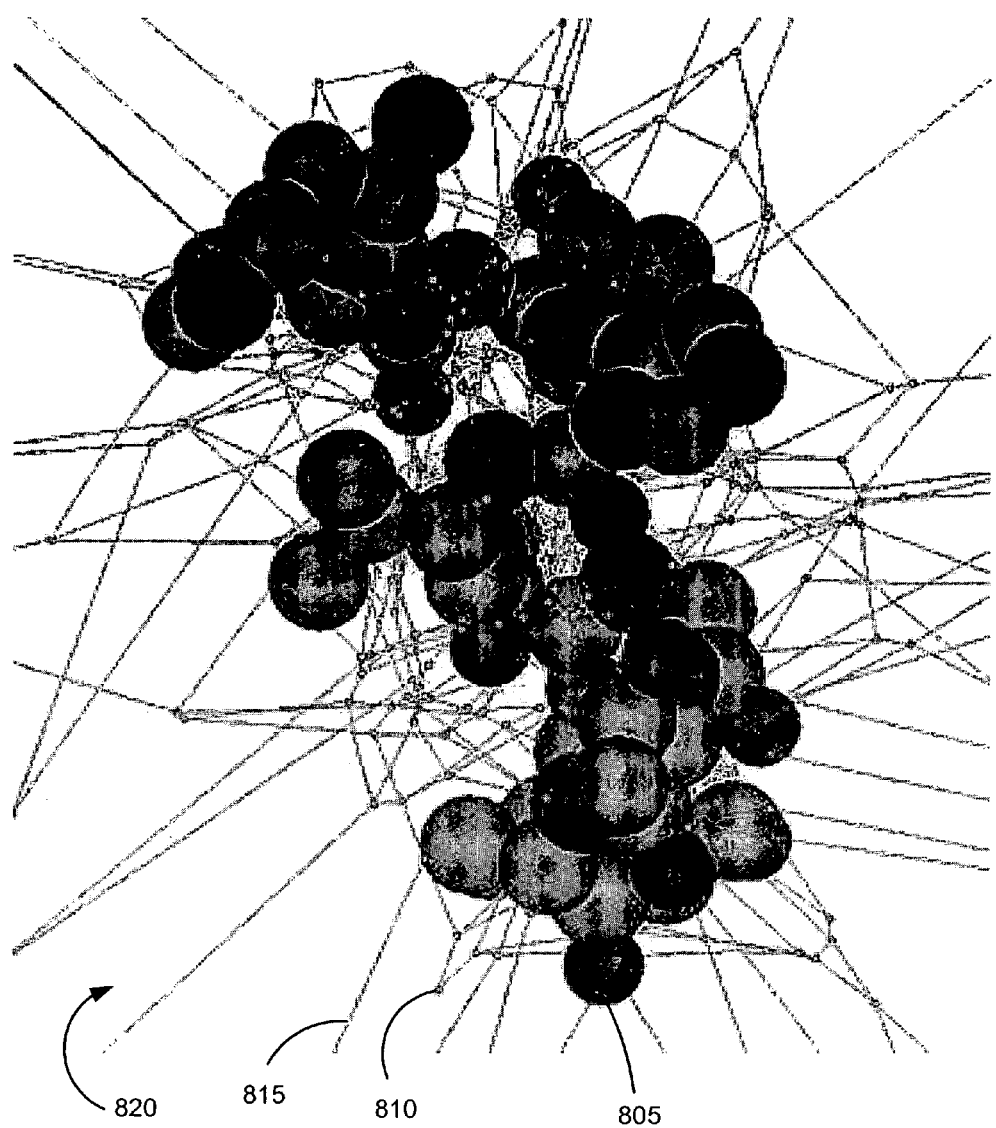
FIG. 8 is a diagram showing a result from a computation of a EVD(S) for a set of spheres representing a subset of a protein from a protein data bank (PDB).

FIG. 8 is a diagram showing a result from a computation of a EVD(S) for a set of spheres representing a subset of a protein from a protein data bank (PDB). The EVD(S) of FIG. 8 can be computed using either the edge-tracing algorithm of FIG. 3 or the region expansion algorithm of FIGS. 4A through 4G. As shown in FIG. 8, the Voronoi diagram includes spheres 805, which represent the molecules and their respective positions in the protein. The resulting Voronoi diagram is shown with the edges 815 that extend to infinity. The faces 820 are shown as clear (as opposed to partially opaque). Each of the vertices 810 are shown as darkened dots.

It should be noted that in order to generate the Voronoi diagram of a protein from the PDB, the data from the PDB may need to be transformed into a format that can readily be processed by the relevant algorithm. For other embodiments of the algorithm, the data can be directly read from the PDB without conversion, depending on the input data structure for the algorithm. In that regard, from the data in the PDB, the structure of the protein can be reconstructed in 3D. When each of the atoms in the protein are approximated as a van der Waals atom, these atoms degenerate into a simple spherical model. Thus, a EVD(S) for the protein can be generated using the above-recited approaches.

Figure 11:
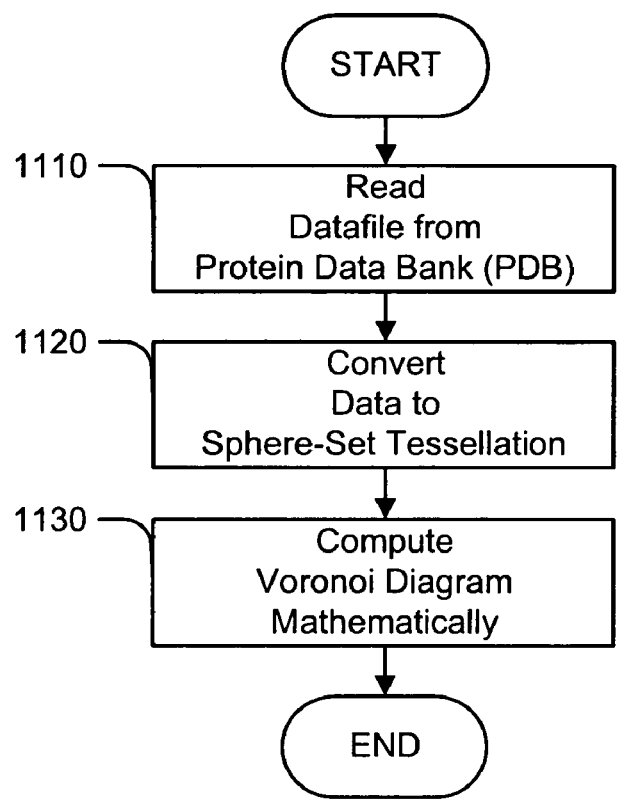
FIG. 11 is a flowchart showing an embodiment of a process for mathematically computing a EVD(S) of a protein structure from a PDB.

FIG. 11 is a flowchart showing an embodiment of a process for mathematically computing a EVD(S) of a protein structure from a PDB. As such, the embodiment of FIG. 11 begins by reading (1110) a data file from a PDB. The read data file is converted (1120) to a sphere-set tessellation, which serves as the input to an algorithm, such as the edge-tracing algorithm or the region-expansion algorithm, as described above. Upon conversion, the EVD(S) of the sphere-set tessellation is mathematically computed (1130).

It has been theorized that the surface of the proteins plays an important role in protein-ligand docking. Having a Voronoi diagram, such as that shown in FIG. 8, can provide relevant information related to drug efficacy. Additionally, the surface analysis can provide useful information on the geometry and topology of an interface between two proteins. Furthermore, such a surface analysis can provide geometrical information that correlates to protein folding or docking mechanisms, including pockets that can act as receptor sites for particular proteins. For ease of viewing and analysis, these surfaces can be rendered, blended, and/or meshed for clearer display.

The topology and geometry information for proteins, as computed using EVD(S) can be useful for extracting docking sites (also called pockets or active sites) on proteins. This information can also be useful for simulating the docking between proteins and ligands during, for example, drug development. Additionally, the topology and geometry information from EVD(S) can be used to study inter-protein interfaces, protein-ligand interfaces, and other molecular interfaces. Moreover, such information can be used to study similarities and differences between molecules and proteins. This information can also be used to search proteins, which have certain structural components, from protein databases (e.g., protein mining). For protein mining applications, multi-resolution modeling of molecules may provide greater efficiency when, for example, EVD(S) is applied for abstraction of molecules with different resolution. It should be appreciated that, once the EVD(S) of various proteins have been computed, a database of the protein EVD(S) can be made available as a library for those who wish to obtain such information.

Protein folding information can also be obtained from the EVD(S) of proteins. Additionally, molecular surface calculations and calculations of other mass properties of molecules, such as, for example, surface area, weight, density, center of gravity, etc. can be obtained from the EVD(S).

Figure 9:
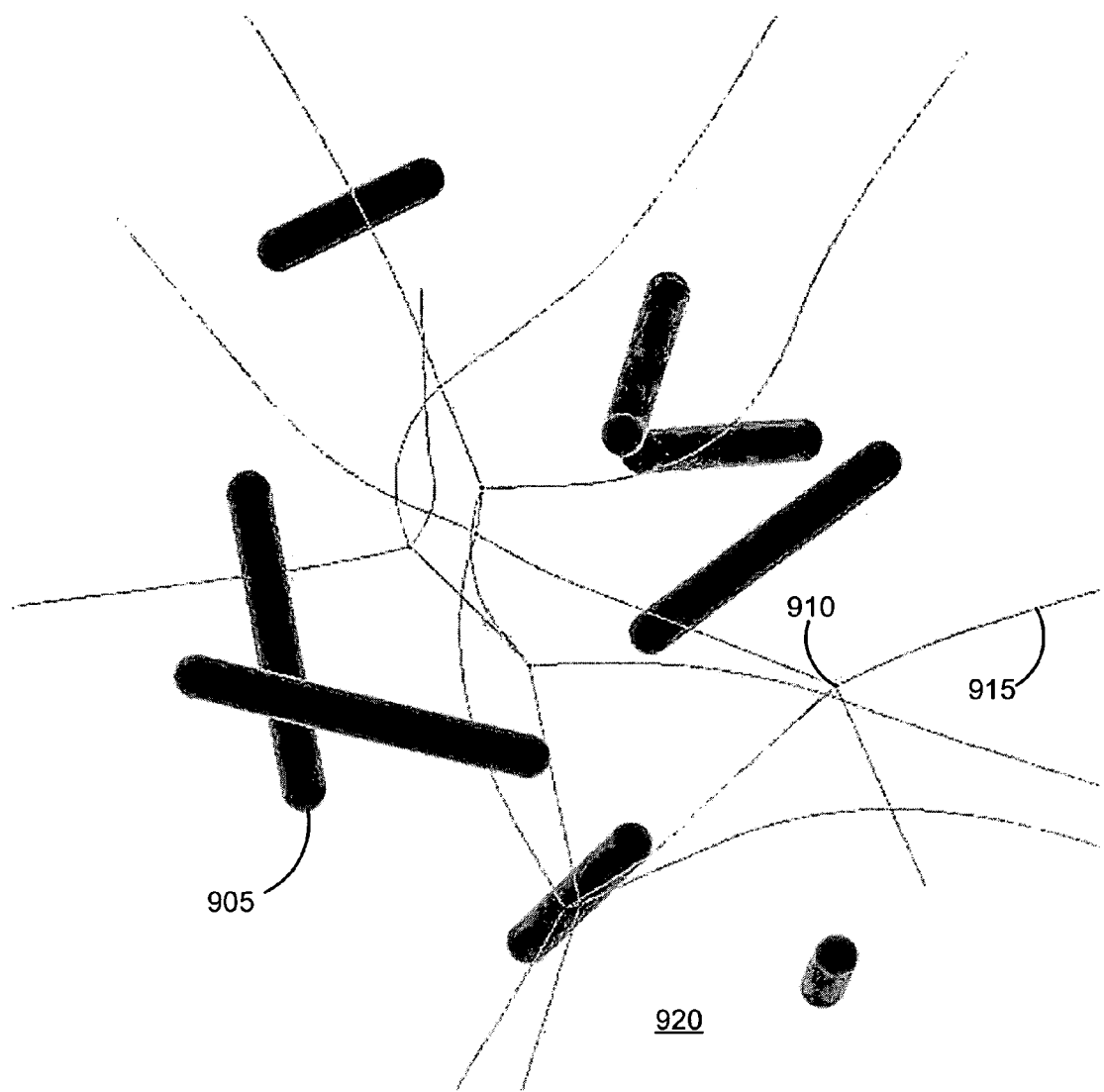
FIG. 9 is a diagram showing a result from a computation of a EVD(S) for a set of convex objects, namely, sphero-cylinders.

FIG. 9 is a diagram showing a result from a computation of a Euclidean Voronoi diagram for a set of convex objects, namely, sphero-cylinders. In general, the Euclidean Voronoi diagram of arbitrary objects is referred to herein as EVD(X). The EVD(X) of FIG. 9 can be computed by modifying the edge-tracing algorithm of FIG. 3 to accommodate non-spherical objects. Alternatively, the EVD(X) of FIG. 9 can be computed by modifying the region-expansion algorithm of FIGS. 4A through 4G to accommodate the non-spherical objects. While convex objects are shown in the embodiment of FIG. 9, it should be appreciated that the algorithm can be extended to non-convex objects, as long as those non-convex objects are amenable to being mathematically defined.

As shown in FIGS. 5 through 9, various topologies and geometries can be analyzed and studied using Voronoi diagrams. Such a tool provides insight into biophysical mechanisms, as well as insights into crystal growth, materials science, and a plethora of other fields. By providing a mathematical approach, as opposed to a numerical approach, greater efficiency can be achieved in computing Voronoi diagrams of 3D objects.

The edge-tracing algorithm of FIG. 3 and the region-expansion algorithm of FIGS. 4A through 4G, which comprise an ordered listing of executable instructions for implementing logical functions, can be embodied in any computer-readable medium for use by or in connection with an instruction execution system, apparatus, or device. Such a system, apparatus, or device may include, for example, a computer-based system, processor-containing system, or other system that can fetch instructions from an instruction execution system, apparatus, or device and execute those instructions. In the context of this document, a "computer-readable medium" can be any means that can contain, store, communicate, propagate, or transport the program for use by, or in connection with, the instruction execution system, apparatus, or device. The computer-readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM or Flash memory) (electronic), an optical fiber (optical), and a portable compact disc read-only memory (CDROM) (optical). Note that the computer-readable medium could even be paper or another suitable medium upon which the program is printed, as the program can be electronically captured via, for instance, optical scanning of the paper or other medium, then compiled, interpreted or otherwise processed in a suitable manner if necessary, and then stored in a computer memory.

The logic components that constitute the edge-tracing algorithm and the region-expansion algorithm may be implemented in hardware, software, firmware, or a combination thereof. In the preferred embodiment(s), the logic components are implemented in software or firmware that is stored in a memory and that is executed by a suitable instruction execution system. If implemented in hardware, as in an alternative embodiment, the logic components can be implemented with any or a combination of the following technologies, Which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Any process descriptions or blocks in flow charts should be understood as representing modules, segments, or portions of code which include one or more executable instructions for implementing specific logical functions or steps in the process, and alternate implementations are included within the scope of the preferred embodiment of the present disclosure in which functions may be executed out of order from that shown or discussed, including substantially concurrently or in reverse order, depending on the functionality involved, as would be understood by those reasonably skilled in the art of the present disclosure.

Although exemplary embodiments have been shown and described, it will be clear to those of ordinary skill in the art that a number of changes, modifications, or alterations to the disclosure as described may be made. For example, while VD(S) is computed in great detail, it should be appreciated that VD(X) can be computed for any "X" that is a mathematically-definable 3D object. For example, X may include cylinders, sphero-cylinders, or other convex 3D structures. Alternatively, X may also include non-convex 3D structures, such as corkscrew patterns, 3D stars, etc. All such changes, modifications, and alterations should therefore be seen as within the scope of the disclosure.

What is claimed is:

1. A computer implemented method for predicting surface interactions between solids comprising:
    using a computer system coupled a database having a first set of spheres, the first set of spheres representing a protein, and a second set of spheres, the second set of spheres representing a ligand, having instructions to create a three-dimensional graphical representation of a set of predicted biological interactions between docking surfaces of the protein and the ligand by:
        accessing the database having a first and second set of spheres;
        mathematically computing a Euclidean Voronoi diagram for the protein based upon the first set of spheres;
        computing a first molecular surface using the mathematically-computed Euclidean Voronoi diagram for the protein;

mathematically computing a Euclidean Voronoi diagram for the ligand based upon the second set of spheres;
computing a second molecular surface using the mathematically-computed Euclidean Voronoi diagram for the ligand; and
determining the set of predicted biological interactions between docking surfaces based on whether a part of the second molecular surface docks into a part of the first molecular surface; and
causing the three-dimensional graphical representation of the set of predicted biological interactions between docking surfaces of the protein and the ligand to be presented on a display apparatus,
wherein mathematically computing the Euclidean Voronoi diagram for the ligand comprises:
finding an initial vertex, the initial vertex being associated with a sphere from the second set of spheres;
generating an edge that emanates from the initial vertex, the edge being mathematically defined; and
computing an empty sphere from the generated edge to define an end vertex of the generated edge.

2. The method of claim 1, further comprising using the computer system coupled to the database having a first set of spheres, the first set of spheres representing a protein, and a second set of spheres, the second set of spheres representing a ligand, having instructions to create a three-dimensional graphical representation of a set of predicted biological interactions between docking surfaces of the protein and the ligand by determining a protein-ligand interface from the first molecular surface and the second molecular surface.

3. The method of claim 1, further comprising using the computer system coupled to the database having a first set of spheres, the first set of spheres representing a protein, and a second set of spheres, the second set of spheres representing a ligand, having instructions to create a three-dimensional graphical representation of a set of predicted biological interactions between docking surfaces of the protein and the ligand by:
determining a topology of the first molecular surface using the mathematically-computed Euclidean Voronoi diagram for the protein; and
determining a topology of the second molecular surface using the mathematically-computed Euclidean Voronoi diagram for the ligand.

4. The method of claim 3, further comprising using the computer system coupled to the database having a first set of spheres, the first set of spheres representing a protein, and a second set of spheres, the second set of spheres representing a ligand, having instructions to create a three-dimensional graphical representation of a set of predicted biological interactions between docking surfaces of the protein and the ligand by:
rendering the determined surfaces; and
displaying the rendered surfaces.

5. The method of claim 3, further comprising using the computer system coupled to the database having a first set of spheres, the first set of spheres representing a protein, and a second set of spheres, the second set of spheres representing a ligand, having instructions to create a three-dimensional graphical representation of a set of predicted biological interactions between docking surfaces of the protein and the ligand by:
blending the determined surfaces; and
displaying the blended surfaces.

6. The method of claim 3, further comprising using the computer system coupled to the database having a first set of spheres, the first set of spheres representing a protein, and a second set of spheres, the second set of spheres representing a ligand, having instructions to create a three-dimensional graphical representation of a set of predicted biological interactions between docking surfaces of the protein and the ligand by:
meshing the determined surfaces; and
displaying the meshed surfaces.

7. A computer implemented method for predicting surface interactions between solids comprising:
using a computer system coupled to a database having a set of spheres representing a protein, having instructions to create a three-dimensional graphical representation of a set of predicted biological characteristics of docking surfaces of the protein by:
accessing the database having a set of spheres representing a protein;
mathematically computing a Euclidean Voronoi diagram based on the set of spheres; and
computing an interface using the mathematically-computed Euclidean Voronoi diagram of the set of spheres; and
causing the three-dimensional graphical representation of a set of predicted biological characteristics of docking surfaces of the protein to be presented on a display apparatus,
wherein mathematically computing an Euclidean Voronoi diagram based on the set of spheres comprises:
finding an initial vertex, the initial vertex begin associated with a sphere from the set of spheres;
generating an edge that emanates from the initial vertex, the edge being mathematically defined; and
computing an empty tangent sphere from the generated edge to define an end vertex of the generated edge.

8. The method of claim 7, further comprising using the computer system coupled to the database having a set of spheres representing a protein, having instructions to create a three-dimensional graphical representation of a set of predicted biological characteristics of docking surfaces of the protein by:
determining a pocket within the protein using the mathematically-computed Euclidean Voronoi diagram; and
predicting a docking structure configured to interface with the determined pocket.

9. A hardware apparatus for predicting surface interactions between solids comprising:
a computer system coupled to a database having a set of spheres representing a protein, having instructions to create a three-dimensional graphical representation of a set of predicted biological characteristics of docking surfaces of the protein configured to:
access the database having a set of spheres representing a protein;
mathematically compute a Euclidean Voronoi diagram based on the set of spheres; and
compute an interface using the mathematically-computed Euclidean Voronoi diagram of the set of spheres,
wherein mathematically computing a Euclidean Voronoi diagram based on the set of spheres comprises:
finding an initial vertex, the initial vertex being associated with a sphere from the set of spheres;
generating an edge that emanates from the initial vertex, the edge being mathematically defined; and
computing an empty tangent sphere from the generated edge to define an end vertex of the generated edge.

* * * * *